(12) United States Patent
Friedman et al.

(10) Patent No.: US 12,708,387 B2
(45) Date of Patent: Aug. 18, 2026

(54) INTRALUMINAL DEVICE WITH VARIABLE WIRE CONFIGURATION

(71) Applicant: RAPID MEDICAL LTD., Yokneam (IL)

(72) Inventors: Aharon Friedman, Haifa (IL); Matan Gedulter, Givat Ela (IL)

(73) Assignee: RAPID MEDICAL LTD., Yokneam (IL)

( * ) Notice: Subject to any disclaimer, the term of this patent is extended or adjusted under 35 U.S.C. 154(b) by 954 days.

(21) Appl. No.: 17/158,762

(22) Filed: Jan. 26, 2021

(65) Prior Publication Data

US 2021/0145466 A1 May 20, 2021

Related U.S. Application Data

(63) Continuation of application No. 17/263,270, filed as application No. PCT/IB2019/000858 on Jul. 23, 2019, now Pat. No. 12,478,395.

(60) Provisional application No. 62/703,795, filed on Jul. 26, 2018.

(51) Int. Cl.
*A61B 17/221* (2006.01)
*A61B 17/00* (2006.01)

(52) U.S. Cl.
CPC .. *A61B 17/221* (2013.01); *A61B 2017/00526* (2013.01); *A61B 2017/2212* (2013.01)

(58) Field of Classification Search
CPC .............................................. A61B 2017/2212
See application file for complete search history.

(56) References Cited

U.S. PATENT DOCUMENTS

| | | | |
|---|---|---|---|
| 5,098,441 A * | 3/1992 | Wechler ............... | A61B 17/221 606/113 |
| 8,715,314 B1 | 5/2014 | Janardhan et al. | |
| 2003/0050663 A1 * | 3/2003 | Khachin .............. | A61B 17/221 606/200 |

(Continued)

FOREIGN PATENT DOCUMENTS

| | | |
|---|---|---|
| CN | 102176870 A | 9/2011 |
| CN | 107205745 A | 9/2017 |

(Continued)

OTHER PUBLICATIONS

First Notification of Office Action and Search Report dated Mar. 1, 2023, for corresponding Chinese Application No. 201980007952.7. (11 pgs.).

(Continued)

*Primary Examiner* — Elizabeth Houston
*Assistant Examiner* — Jonathan A Hollm
(74) *Attorney, Agent, or Firm* — The Roy Gross Law Firm, LLC; Roy D. Gross

(57) ABSTRACT

Intraluminal devices and methods of fabricating intraluminal devices may be provided. In one implementation, an intraluminal device may be formed of a plurality of wires and may include a distal coil, a proximal coil, and an expandable mesh segment positioned between the distal and proximal coils. The proximal coil may include more wires of the plurality of wires than the distal coil and the expandable mesh segment. Due to the smaller number of wires forming the distal coil, the intraluminal device may be configured to have a soft and atraumatic distal tip and a more rigid proximal cable.

15 Claims, 14 Drawing Sheets

(56) References Cited

U.S. PATENT DOCUMENTS

2003/0153971 A1 8/2003 Chandrasekaran
2004/0082879 A1* 4/2004 Klint .................. A61B 17/1214 600/585
2005/0043756 A1 2/2005 Lavelle et al.
2011/0224707 A1 9/2011 Miloslavski et al.
2011/0288572 A1 11/2011 Martin
2016/0039098 A1 2/2016 Sanders et al.
2016/0058458 A1* 3/2016 Hansen ................ A61B 17/221 606/200
2016/0081825 A1* 3/2016 Sudin ............... A61B 17/12031 28/165
2016/0302908 A1 10/2016 Tafti et al.
2017/0020542 A1 1/2017 Martin et al.
2017/0119409 A1 5/2017 Ma

FOREIGN PATENT DOCUMENTS

EP 2713909 B1 7/2018
WO WO 2016/125018 A2 8/2016
WO WO-2017077393 A1 * 5/2017 ............... A61F 2/01
WO WO 2018/078452 A1 5/2018
WO WO 2018/109566 A2 6/2018

OTHER PUBLICATIONS

Extended European Search Report dated Mar. 24, 2022, issued by the European Patent Office in counterpart European Patent Application No. 19840762.9 (10 pages).
International Search Report and Written Opinion of the International Searching Authority from the U.S. Patent and Trademark Office for International Application No. PCT/IB2019/000858, mailed Jan. 14, 2020 (18 pages).

* cited by examiner

INTRALUMINAL DEVICE WITH VARIABLE WIRE CONFIGURATION

CROSS-REFERENCE TO RELATED APPLICATIONS

This application is a continuation of U.S. patent application Ser. No. 17/263,270, filed Jan. 26, 2021, now pending, which is a U.S. national stage entry under 35 U.S.C. § 371 of International Application No. PCT/IB2019/000858, filed Jul. 23, 2019, which claims the benefit of priority from U.S. Provisional Application No. 62/703,795, filed Jul. 26, 2018, all of which are hereby incorporated by reference in their entireties.

TECHNICAL FIELD

This disclosure relates to intravascular and intraluminal medical devices and systems configured to retrieve an obstruction from human blood vessels, such as a clot. The disclosure also relates to methods of manufacturing intravascular and intraluminal medical devices and systems.

BACKGROUND

Intravascular and intraluminal medical devices are commonly used to treat a variety of medical conditions in hollow body organs such as blood vessels. For example, inflatable or expandable devices can be utilized to dilate constricted body vessels or to provide support to injured or occluded body lumens. Intravascular and intraluminal devices can also be utilized to capture and remove obstructions, such as clots or stones, from body lumens. For example, wire mesh devices can be expanded within intravascular occlusions to penetrate and/or capture occlusions.

Some vasculature, such as intracranial vasculature, includes vessels that are both narrow and tortuous. When an occlusion or stenosis occurs in the intracranial vasculature, an intravascular treatment device can be passed through the tortuous anatomy to reach the treatment site. While these treatment devices must have sufficiently small diameters so as to fit through the narrow vessels, they must also be both rigid enough to perform the desired operation at a treatment site and sufficiently pliable so as to be capable of being maneuvered to the treatment site with a minimum of complications. Complications can include, among other things, difficulty in delivering the device to a treatment site through a tortuous path, as well as the potential for damage to healthy vessel walls as a result of an intracranial and intraluminal device that is too rigid.

This disclosure is directed to an improved device and system that exhibits sufficient rigidity in the operative portions thereof to perform therapeutic operations such as vessel dilation or clot capture at remote body sites, but which also exhibits a sufficiently pliable distal tip in order to avoid potential complications as the device is delivered to a treatment site.

SUMMARY

Disclosed herein are intraluminal devices with sufficient rigidity in operative portions thereof to perform therapeutic operations at remote body sites, but which also exhibit sufficiently pliable distal tips to avoid potential complications from insertion of such devices into the body. Also disclosed herein are manufacturing methods of such intraluminal devices.

According to an exemplary embodiment of the present disclosure, an intraluminal device including an elongated body formed of a plurality of wires is provided. The intraluminal device includes a first region wherein the plurality of wires are twisted to form a first cable. The intraluminal device also includes a second region, distal to the first region, in which the plurality of wires are woven to form an expandable mesh segment which is configured to capture a blood clot. The intraluminal device also includes a third region distal to the second region and forming a distal tip of the elongated body, wherein the plurality of wires in the third region are twisted to form a second cable. At least one wire of the plurality of wires extends continuously from the first region to the distal tip of the elongated body.

The expandable mesh segment includes at least one expandable filter segment in which the plurality of wires are woven to form a first weave pattern, the first weave pattern having an opening therein formed between two or more wires. The expandable mesh segment also includes at least one expandable clot capture zone in which the plurality of wires are woven to form a second weave pattern, the second weave pattern being different from the first weave pattern and having an opening therein formed between two or more wires. In an expanded configuration, the opening of the at least one clot capture zone is larger than the opening of the at least one filter segment. The plurality of wires in the at least one clot capture zone are grouped into a plurality of wire groupings in the at least one clot capture zone, wherein each wire grouping of the plurality of wire groupings includes at least two wires and forms an intertwined wire combination. The opening of the at least one clot capture zone is formed between at least two of the intertwined wire combinations. Each wire grouping of the plurality of wire groupings includes one wire, two wires, three wires, or four wires. The at least one expandable filter segment is configured to capture smaller clots than the at least one expandable clot capture zone. The expandable mesh segment includes a first filter segment, a second filter segment distal to the first filter segment, a first clot capture zone positioned between the first filter segment and the first region of the intraluminal device, and a second clot capture zone positioned between the second filter segment and the third region of the intraluminal device. The plurality of wires includes of at least one of the set of: eight wires, ten wires, and twelve wires. The at least one wire has a diameter between 40 microns and 200 microns. For example, the at least one wire can have a diameter that is at least one of: 40 microns, 45 microns, 50 microns, 55 microns, 60 microns, 65 microns, 70 microns, 75 microns, 80 microns, 85 microns, 90 microns, 95 microns, 100 microns, 105 microns, 110 microns, 115 microns, 120 microns, 125 microns, 130 microns, 135 microns, 140 microns, 145 microns, 150 microns, 155 microns, 160 microns, 165 microns, 170 microns, 175 microns, 180 microns, 185 microns, 190 microns, 195 microns, and 200 microns, or a range thereof. For example, the at least one wire can have a diameter in a range between 50 microns and 75 microns. The intraluminal device also includes at least one radiopaque marker positioned at a point along the elongated body, the point along the elongated body being at least one of: a point distal to the second region and a point proximal of the second region. The first region of the intraluminal device, the second region of the intraluminal device, and the third region of the intraluminal device are formed as a single unitary structure.

According to another exemplary embodiment of the present disclosure, a method of manufacturing an intraluminal device including an elongated body formed of a plurality of wires is provided. The method includes twisting a plurality of wires upon a first segment of a mandrel so as to form a first cable of the elongated body. The method also includes weaving the plurality of wires upon a second segment of the mandrel so as to form an expandable mesh segment of the elongated body which is configured to capture a blood clot. The method also includes twisting the plurality of wires upon a third segment of the mandrel so as to form a second cable of the elongated body. The second segment of the mandrel is positioned between the first segment of the mandrel and the third segment of the mandrel.

The method also includes heat-treating the expandable mesh segment. The second segment of the mandrel has a larger diameter than the first segment of the mandrel and the third segment of the mandrel. The plurality of wires includes of at least one of the set of: eight wires, ten wires, and twelve wires. At least one wire of the plurality of wires has a diameter between 40 microns and 200 microns. For example, the at least one wire can have a diameter that is at least one of: 40 microns, 45 microns, 50 microns, 55 microns, 60 microns, 65 microns, 70 microns, 75 microns, 80 microns, 85 microns, 90 microns, 95 microns, 100 microns, 105 microns, 110 microns, 115 microns, 120 microns, 125 microns, 130 microns, 135 microns, 140 microns, 145 microns, 150 microns, 155 microns, 160 microns, 165 microns, 170 microns, 175 microns, 180 microns, 185 microns, 190 microns, 195 microns, and 200 microns, or a range thereof. For example, the at least one wire of the plurality of wires can have a diameter in a range between 50 microns and 75 microns. The first cable of the elongated body, the expandable mesh segment of the elongated body, and the second cable of the elongated body are formed as a single unitary structure.

According to a further exemplary embodiment of the present disclosure, an intraluminal device including an elongated body formed of a plurality of wires is provided. The intraluminal device includes a first region wherein the plurality of wires are twisted to form a first cable. The intraluminal device also includes a second region, distal to the first region, in which the plurality of wires are woven to form an expandable mesh segment which is configured to capture a blood clot. The intraluminal device also includes a third region distal to the second region and forming a distal tip of the elongated body, wherein the plurality of wires in the third region are twisted to form a second cable. The second cable is configured to be more pliable than the first cable.

At least one wire of the plurality of wires has a diameter between 40 microns and 200 microns. For example, the at least one wire can have a diameter that is at least one of: 40 microns, 45 microns, 50 microns, 55 microns, 60 microns, 65 microns, 70 microns, 75 microns, 80 microns, 85 microns, 90 microns, 95 microns, 100 microns, 105 microns, 110 microns, 115 microns, 120 microns, 125 microns, 130 microns, 135 microns, 140 microns, 145 microns, 150 microns, 155 microns, 160 microns, 165 microns, 170 microns, 175 microns, 180 microns, 185 microns, 190 microns, 195 microns, and 200 microns, or a range thereof. For example, the at least one wire of the plurality of wires can have a diameter in a range between 50 microns and 75 microns. The second cable is configured to have a smaller cable coiling angle than the first cable. The second cable contains fewer wires than the first cable. The second cable is treated to reduce diameters of the portions of the plurality of wires therein.

According to a still further exemplary embodiment of the present disclosure, an intraluminal device including an elongated body formed of a plurality of wires is provided. The intraluminal device includes a first region wherein the plurality of wires are twisted to form a first cable. The intraluminal device also includes a second region, distal to the first region, in which the plurality of wires are woven to form an expandable mesh segment. The intraluminal device also includes a third region distal to the second region and forming a distal tip of the elongated body, wherein the plurality of wires in the third region are twisted to form a second cable. The plurality of wires in the expandable mesh segment are grouped into a plurality of wire pairs in the expandable mesh segment, wherein each wire pair of the plurality of wire pairs forms an intertwined wire combination. At least a first wire pair of the plurality of wire pairs and at least a second wire pair of the plurality of wire pairs form a crossing in the expandable mesh segment, at least one wire of the first wire pair passing between each wire of the second wire pair at the crossing.

The first wire pair of the plurality of wire pairs includes at least a first pairwise twist proximal to the crossing and includes at least a second pairwise twist distal to the crossing. At least one wire of the second wire pair passes between each wire of the first wire pair at the crossing. At least one wire of the first wire pair does not pass between the wires of the second wire pair at the crossing. At least one wire of the second wire pair does not pass between the wires of the first wire pair at the crossing.

According to another exemplary embodiment of the present disclosure, an intraluminal device including an elongated body formed of a plurality of wires is provided. The intraluminal device includes a first region wherein the plurality of wires are twisted to form a first cable. The intraluminal device also includes a second region, distal to the first region, in which the plurality of wires are woven to form an expandable mesh segment which is configured to capture a blood clot. The intraluminal device also includes a third region distal to the second region and forming a distal tip of the elongated body, wherein the plurality of wires in the third region are twisted to form a second cable. The first region includes of more wires than one or more of the second region and the third region.

The second region includes of the same number of wires as the third region. The second region includes of more wires than the third region. The first region includes eleven wires, the second region includes eight wires, and the third region includes eight wires. The first region includes twelve wires, the second region includes eight wires, and the third region includes eight wires. At least one wire of the plurality of wires extends continuously from the first region to the third region. The first region of the intraluminal device, the second region of the intraluminal device, and the third region of the intraluminal device are formed as a single unitary structure.

According to a further exemplary embodiment of the present disclosure, a method of manufacturing an intraluminal device including an elongated body formed of a plurality of wires is provided. The method includes twisting a plurality of wires upon a first segment of a mandrel so as to form a first cable of the elongated body. The method also includes cutting at least one wire of the plurality of wires at a distal end of the first cable. The method also includes weaving the remaining wires of the plurality of wires upon a second segment of the mandrel so as to form an expandable mesh segment of the elongated body which is configured to capture a blood clot. The method also includes twisting the remaining wires of the plurality of wires upon a third segment of the mandrel so as to form a second cable of the elongated body. The second segment of the mandrel is positioned between the first segment of the mandrel and the third segment of the mandrel.

The method also includes cutting at least one wire of the plurality of wires at a distal end of the expandable mesh segment. The method also includes heat-treating the expandable mesh segment.

The second segment of the mandrel has a larger diameter than the first segment of the mandrel and the third segment of the mandrel. The plurality of wires includes of eight wires, ten wires, or twelve wires. At least one wire of the plurality of wires has a diameter between 40 microns and 200 microns. For example, the at least one wire can have a diameter that is at least one of: 40 microns, 45 microns, 50 microns, 55 microns, 60 microns, 65 microns, 70 microns, 75 microns, 80 microns, 85 microns, 90 microns, 95 microns, 100 microns, 105 microns, 110 microns, 115 microns, 120 microns, 125 microns, 130 microns, 135 microns, 140 microns, 145 microns, 150 microns, 155 microns, 160 microns, 165 microns, 170 microns, 175 microns, 180 microns, 185 microns, 190 microns, 195 microns, and 200 microns, or a range thereof. For example, the at least one wire of the plurality of wires can have a diameter in a range between 50 microns and 75 microns. The first cable of the elongated body, the expandable mesh segment of the elongated body, and the second cable of the elongated body are formed as a single unitary structure.

According to a further exemplary embodiment of the present disclosure, an intraluminal device including an elongated body formed of a plurality of wires is provided. The intraluminal device includes a first region wherein the plurality of wires are twisted to form a first cable; a second region, distal to the first region, in which the plurality of wires are woven to form an expandable mesh segment; and a third region distal to the second region and forming a distal tip of the elongated body, wherein the plurality of wires in the third region are twisted to form a second cable. The plurality of wires in the expandable mesh segment includes a first group of wires and a second group of wires. The first group of wires includes two wires and the second group of wires includes three wires. Each wire of the plurality of wires includes a first side surface and a second side surface opposite of the first side surface. A first wire of the first group of wires is configured to cross the first side surfaces of both a first wire of the second group of wires and a second wire of the second group of wires. The first wire of the first group of wires is configured to cross the second side surface of a third wire of the second group of wires. A second wire of the first group of wires is configured to cross the second side surfaces of both the first wire of the second group of wires and the second wire of the second group of wires. The second wire of the first group of wires is configured to cross the first side surface of the third wire of the second group of wires.

According to a further exemplary embodiment of the present disclosure, an intraluminal device including an elongated body formed of a plurality of wires is provided. The intraluminal device includes a first region wherein the plurality of wires are twisted to form a first cable; a second region, distal to the first region, in which the plurality of wires are woven to form an expandable mesh segment; and a third region distal to the second region and forming a distal tip of the elongated body, wherein the plurality of wires in the third region are twisted to form a second cable. The plurality of wires in the expandable mesh segment includes a first group of wires and a second group of wires. The first group of wires includes two wires. The second group of wires includes three wires. Each wire of the plurality of wires includes a first side surface and a second side surface opposite of the first side surface. A first wire of the first group of wires is configured to cross the first side surface of a first wire of the second group of wires and to cross the second side surfaces of both a second wire of the second group of wires and third wire of the second group of wires. A second wire of the first group of wires is configured to cross the first side surfaces of each wire in the second group of wires.

According to a further exemplary embodiment of the present disclosure, an intraluminal device including an elongated body formed of a plurality of wires is provided. The intraluminal device includes a first region wherein the plurality of wires are twisted to form a first cable; a second region, distal to the first region, in which the plurality of wires are woven to form an expandable mesh segment; and a third region distal to the second region and forming a distal tip of the elongated body, wherein the plurality of wires in the third region are twisted to form a second cable. The plurality of wires in the expandable mesh segment includes a first group of wires and a second group of wires. The first group of wires includes three wires and the second group of wires includes three wires. Each wire of the plurality of wires includes a first side surface and a second side surface opposite of the first side surface. A first wire of the first group of wires is configured to cross the first side surface of a first wire of the second group of wires and to cross the second side surfaces of both a second wire of the second group of wires and third wire of the second group of wires. A second wire of the first group of wires is configured to cross the first side surface of the first wire of the second group of wires and to cross the second side surfaces of both the second wire of the second group of wires and third wire of the second group of wires. A third wire of the first group of wires is configured to cross the first side surfaces of each wire in the second group of wires.

According to a further exemplary embodiment of the present disclosure, an intraluminal device including an elongated body formed of a plurality of wires is provided. The intraluminal device includes a first region wherein the plurality of wires are twisted to form a first cable; a second region, distal to the first region, in which the plurality of wires are woven to form an expandable mesh segment; and a third region distal to the second region and forming a distal tip of the elongated body, wherein the plurality of wires in the third region are twisted to form a second cable. The plurality of wires in the expandable mesh segment are grouped into a plurality of wire groups in the expandable mesh segment. Each wire group of the plurality of wire groups forms a crossing in the expandable mesh segment with another wire group of the plurality of wire groups. A first wire group of the plurality of wire groups includes three wires forming a twisting structure in which each of the three wires wraps about the other two wires of the three wires. The twisting structure of the first wire group is positioned in a segment of the expandable mesh segment between two adjacent crossings of the first wire group.

According to a further exemplary embodiment of the present disclosure, an intraluminal device including an elongated body formed of a plurality of wires is provided. The intraluminal device includes a first region wherein the plurality of wires are twisted to form a first cable; a second region, distal to the first region, in which the plurality of wires are woven to form an expandable mesh segment; and a third region distal to the second region and forming a distal tip of the elongated body, wherein the plurality of wires in the third region are twisted to form a second cable. The plurality of wires in the expandable mesh segment are grouped into a plurality of wire groups in the expandable mesh segment. Each wire group of the plurality of wire groups forms a crossing in the expandable mesh segment with another wire group of the plurality of wire groups. A first wire group of the plurality of wire groups includes three wires. A first wire of the three wires and a second wire of the three wires forms a twisting structure in which each of the first and second wires wraps about the other. A third wire of the three wires is free from twisting with the first wire and second wire in the twisting structure. The twisting structure is positioned in a segment of the expandable mesh segment between two adjacent crossings of the first wire group.

According to a further exemplary embodiment of the present disclosure, an intraluminal device including an elongated body formed of a plurality of wires is provided. The intraluminal device includes a first region wherein the plurality of wires are twisted to form a first cable; a second region, distal to the first region, in which the plurality of wires are woven to form an expandable mesh segment; and a third region distal to the second region and forming a distal tip of the elongated body, wherein the plurality of wires in the third region are twisted to form a second cable. The plurality of wires in the expandable mesh segment are grouped into a plurality of wire groups in the expandable mesh segment. Each wire group of the plurality of wire groups forms a crossing in the expandable mesh segment with another wire group of the plurality of wire groups. A first wire group of the plurality of wire groups includes three wires. Each of the three wires has a first side surface and a second side surface opposite of the first side surface. The first wire group forms an interlocking structure in a segment of the expandable mesh segment between two adjacent crossings of the first wire group. Within the interlocking structure, a first wire of the first wire group is configured to cross the first side surface of a second wire of the first wire group and to cross the second side surface of a third wire of the first wire group. Within the interlocking structure, the second wire of the first wire group does not contact the third wire of the first wire group.

DETAILED DESCRIPTION

Exemplary embodiments are described with reference to the accompanying drawings. In the figures, which are not necessarily drawn to scale, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used herein and in the appended claims, the singular forms "a," "an," and "the" include plural references unless the context clearly dictates otherwise.

Embodiments of the present disclosure relate generally to medical devices and methods for treating occlusions in a body. More particularly, embodiments of the present disclosure relate to devices and method for removing clots, including, but not limited to, emboli and thrombi from blood vessels. Additionally or alternatively, embodiments of the present disclosure may also be utilized to dilate occluded hollow body organs, as well as in other medical procedures where removal of a blockage or a foreign body is desired.

In accordance with embodiments of the present disclosure, there may be provided an intraluminal device including an expandable clot engaging component. An expandable clot engaging component may have a mesh or stent-like structure and may be configured, upon deployment and expansion within a hollow body organ such as a blood vessel, to catch, retain, and remove a blood clot or other obstruction.

Figure 1:
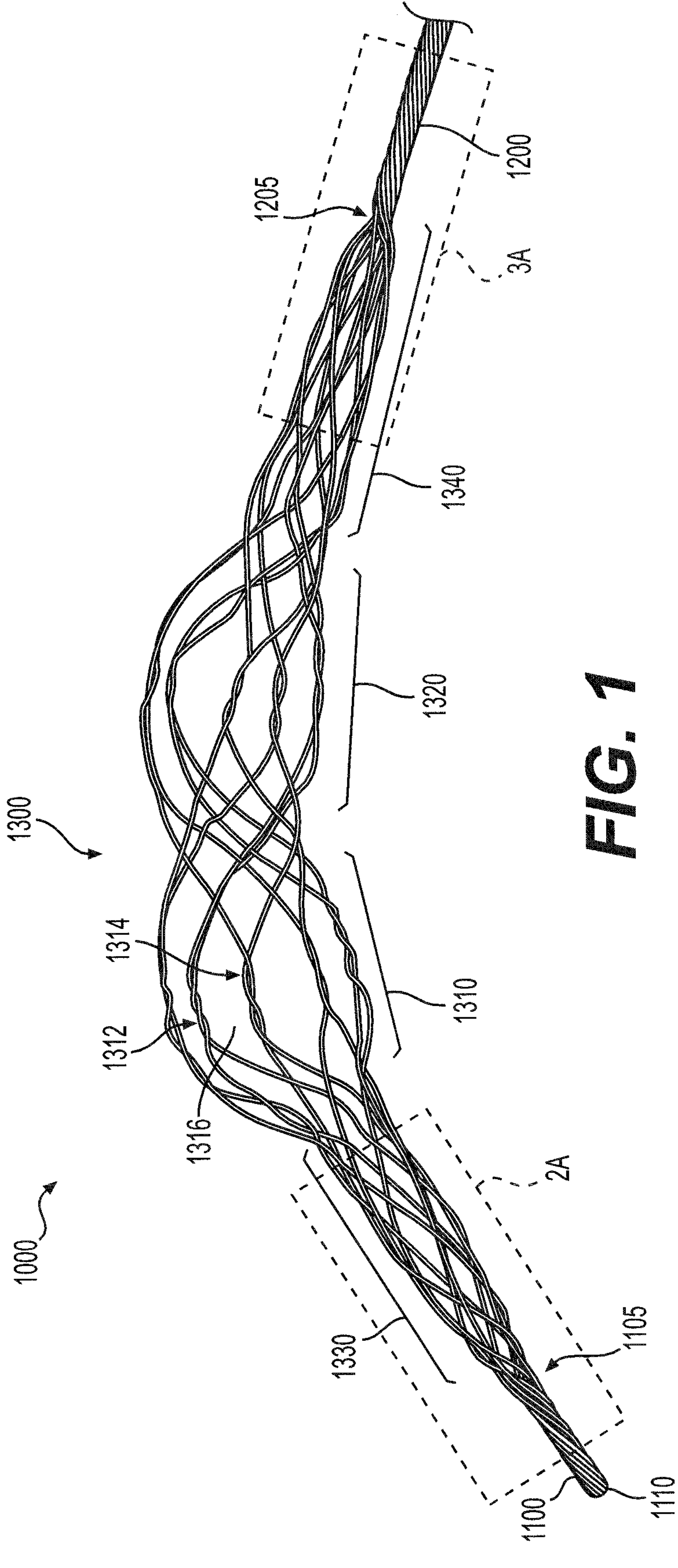
FIG. 1 illustrates an exemplary intraluminal device, consistent with various embodiments of the present disclosure.

FIG. 1 illustrates an exemplary intraluminal device 1000. Device 1000 may include a distal cable 1100, a proximal cable 1200, and an expandable clot engaging component 1300 therebetween. In the present disclosure, the term "proximal" refers to the end of a device (e.g. device 1000) which is closer to the device operator during use, and the term "distal" refers to the end of a device which is further from the device operator during use. Device 1000 may include a plurality of wires or filaments extending from proximal cable 1200, through clot engaging component 1300, to distal cable 1100. Device 1000 may include eight wires, nine wires, ten wires, eleven wires, twelve wires, or any other suitable number of wires. Without limitation, for example, the device 1000 can include six wires, seven wires, eight wires, nine wires, ten wires, eleven wires, twelve wires, thirteen wires, fourteen wires, fifteen wires, sixteen wires, seventeen wires, or eighteen wires. In some embodiments, the plurality of wires may be coiled about a cable axis to form the distal cable 1100 and proximal cable 1200; as a result, the cables may be configured to maintain a constant diameter during expansion and contraction of clot engaging component 1300. Distal cable 1100 may include distal tip 1110, which may be rounded or otherwise shaped so as to render the tip 1110 atraumatic to tissue. In some embodiments, proximal cable 1200 may extend proximally from the clot engaging component 1300 to a control handle (not pictured). Alternatively, device 1000 may also include a tubular shaft positioned proximal to the proximal cable 1200 and extending between proximal cable 1200 and the control handle.

In some embodiments, the wires may have a diameter of between 40 microns and 200 microns. Without limitation, for example, the diameter of a wire in device 1000 can be any one of: 40 microns, 45 microns, 50 microns, 55 microns, 60 microns, 65 microns, 70 microns, 75 microns, 80 microns, 85 microns, 90 microns, 95 microns, 100 microns, 105 microns, 110 microns, 115 microns, 120 microns, 125 microns, 130 microns, 135 microns, 140 microns, 145 microns, 150 microns, 155 microns, 160 microns, 165 microns, 170 microns, 175 microns, 180 microns, 185 microns, 190 microns, 195 microns, and 200 microns, or a range thereof. For example, the wires may have a diameter in a range between 50 microns and 75 microns. Advantageously, wires with a diameter between 50 microns and 75 microns may allow distal cable 1100 to be pliable and atraumatic to tissue during use, while still providing sufficient rigidity to device 1000 for therapeutic use within the body.

In some embodiments, the plurality of wires may be braided in the clot engaging component 1300 to form an expandable mesh-like or stent-like structure. Within the mesh-like structure, the plurality of wires may be woven to cross one another without being connected, whereby the wires may be configured to move relative to one another. In some embodiments, the wires may be crossed and bent to form the mesh-like structure such that the proximal and distal ends of the clot engaging component 1300 may be free of exposed ends of wires; the absence of exposed ends may result in reduced trauma to the anatomy.

Clot engaging component 1300 may be configured to radially expand and contract;

accordingly, clot engaging component 1300 may be configured to transition between a radially contracted configuration and a radially expanded configuration. In some embodiments, clot engaging component 1300 may be self-expanding due to, at least in part, the arrangement and material composition of the plurality of wires. For example, intraluminal device 1000 may be delivered to a treatment site within a delivery sheath (not pictured), which may retain clot engaging component 1300 in the contracted configuration. Movement of the device 1000 relative to the sheath (e.g. distal retraction of the sheath) may free the device 1000 and allow expansion of the clot engaging component 1300.

Additionally or alternatively, device 1000 may include at least one elongated control member (not pictured) which may control expansion and contraction of clot engaging component 1300. The control member may include a wire or filament connected to, interwoven with, looped and/or knotted around distal cable 1100 and/or to a distal end of clot engaging component 1300. The control member may pass either within or parallel to clot engaging component 1300 and proximal cable 1200 to the control handle, where a device operator may utilize the control member to expand or contract clot engaging component 1300. The control member may be configured to apply force to a portion of device 1000 to affect expansion or contraction of clot engaging component 1300. For example, the control member may be configured to exert a proximally-directed force on the distal end of clot engaging component 1300, causing the clot engaging component to radially expand. Similarly, the control member may be configured to exert a distally-directed force on the distal end of clot engaging component 1300, causing the clot engaging component to radially contract.

The plurality of wires of intraluminal device 1000 may be constructed of any suitable flexible material known to those skilled in the art. Suitable flexible materials can include, but are not limited to, polymers, metals, metal alloys, and combinations therefore. In some embodiments, for example, the wires may be constructed from super elastic metals such as Nitinol. In order to visualize the clot engaging component 1300 with angiographic imaging, the wires may further include a radio-opaque marker and/or material. For example, in an embodiment, device 1000 may include a plurality of Nitinol wires with a core made of Tantalum or Platinum metals. The radiopaque core can be 20% to 50% by volume (e.g. 30% or 40%). In an additional embodiment, the wires can be made to be radiopaque by deposition of a thin layer of radiopaque metal such as Platinum. In some embodiments, such radiopaque features may be positioned at the proximal and distal ends of clot engaging component 1300 in FIG. 1.

As previously mentioned, a delivery sheath may be provided. The sheath may be a hollow tubular structure configured to receive at least a portion of intraluminal device 1000 therein, thus surrounding and radially compressing the device, including clot engaging component 1300. The sheath may be removable from device 1000 to thereby enable the clot engaging component 1300 to radially expand in a blood vessel in which the sheath is deployed. In some embodiments, device 1000 may be delivered to a treatment site (e.g. a clot site) within the sheath. The sheath may be configured to allow for controlled expansion and contraction of clot engaging component 1300. For example, as previously discussed, clot engaging component 1300 may be configured to radially expand upon removal of the sheath (e.g. when the sheath is retracted proximally). In addition, device 1000 may be returned into the sheath (e.g. by pulling device 1000 proximally into the sheath), causing clot engaging component 1300 to return to the contracted configuration.

Intraluminal device 1000 may be configured to capture obstructions such as blood clots and to remove them from the body. Additionally or alternatively, device 1000 may be configured to exert an outward force on the walls of hollow body organs, such as blood vessels. In some embodiments, clot engaging component 1300 may be configured to exhibit a substantially uniform shape when in the expanded configuration. Alternatively, as depicted in FIG. 1, clot engaging component 1300 may be configured to exhibit a substantially asymmetrical shape when in the expanded configuration. Consistent with the disclosure, an asymmetrical shape may improve the ability of clot engaging component 1300 to comply with the anatomy of a blood vessel.

In some embodiments, at least a portion of clot engaging component 1300 may be configured to expand to approximately an inner diameter of the blood vessel at a blood clot site. Expansion to approximately the inner diameter of the blood vessel may result in clot engaging component 1300 exerting a force on the vessel wall, causing separation of a clot from the vessel wall. Advantageously, separation of the clot from the vessel wall may reduce the amount of force required to further remove the clot from the vessel wall and mitigate the tendency of clots to break into multiple fragments during removal from the blood vessel. In the contracted configuration, clot engaging component 1300 may exert a force upon clots contained therein, retaining the clots within intraluminal device 1000 and mitigating the tendency of the clots to fragment. The clots may then be retrieved from the vessel, with the clots retained solely within the clot engaging component 1300. Alternatively, for clots small enough to fit within the delivery sheath, the clots may be pulled into the delivery sheath before removal from the vessel. In this manner, the delivery sheath may exert further holding force on the clot.

In some embodiments, clot engaging component 1300 may include one or more clot capture zones 1310, 1320, a distal filter 1330, and/or a proximal filter 1340, each having a weave pattern of the wires extending therethrough. In the example of FIG. 1, clot engaging component 1300 includes two clot capture zones, a distal filter, and a proximal filter. However, in alternative embodiments a clot engaging component may not include one or more of a capture zone, a distal filter, and a proximal filter. In addition, in alternative embodiments a clot engaging component may include one, three, four, five or more clot capture zones. Proximal filter 1340 may intersect with proximal sheath 1200 at transition 1205, with the plurality of wires extending therebetween. Similarly, distal filter 1330 may intersect with distal sheath 1100 at transition 1105, with the plurality of wires extending therebetween. Capture zones 1310, 1320 may be positioned between the proximal and distal filters, and may have a larger diameter than the proximal and distal filters when clot engaging component 1300 is in the expanded configuration. In some embodiments, both capture zones may have the same diameter when expanded; alternatively, one capture zone may have a larger diameter than the other when expanded. Capture zones 1310, 1320 may have the same or different wire weave patterns. For example, one or more of capture zones 1310, 1320 may have a wire weave pattern in which at least two of the plurality of wires may be coiled around one another to form intertwined wire combinations, such as twists 1312 and 1314 in FIG. 1. In the example of FIG. 1, two wires are coiled together to form twists; however, in alternative embodiments three or more wires may be coiled together to form the twists of the one or more capture zones. The twists of wires may prevent slippage of the wires (e.g. during clot engaging component 1300 expansion and contraction) and may form large clot capturing windows 1316 therebetween. Windows 1316 may capture and retain larger clots and other obstructions. Distal filter 1330 and proximal filter 1340 may have the same or different wire weave patterns, which may be different from the weave patterns of capture zones 1310, 1320. The weave pattern of one or more of distal filter 1330 and proximal filter 1340 may provide structural support for capture zones 1310, 1320. In addition, the openings between the wires in the distal and proximal filters may be smaller than clot capturing windows 1316; accordingly, distal filter 1330 and proximal filter 1340 may be configured to capture and retain obstructions which may be too small to be captured by zones 1310, 1320.

In some embodiments, one or more of the plurality of wires may extend continuously through proximal cable 1200, clot engaging component 1300, and distal cable 1100, without connections or attachments (e.g. welding or gluing) to other wires in adjacent segments. That is, the length of one or more of the wires may extend from the distal end of the device 1000 to the proximal end of the device 1000. For example, in some embodiments all of the wires of device 1000 may extend continuously from the distal end of the device 1000 to the proximal end of the device 1000. As a result, and where each of the wires of the plurality of wires is configured to extend continuously through proximal cable 1200, clot engaging component 1300, and distal cable 1100 as described above, proximal cable 1200, clot engaging component 1300, and distal cable 1100 can be manufactured as a single unitary structure, and, accordingly, proximal cable 1200, clot engaging component 1300, and distal cable 1100 would not be manufactured separately and welded, glued, or otherwise attached together. This configuration is illustrated in FIGS. 1-3B: each of the plurality of wires may pass continuously along the length of intraluminal device 1000, including through transitions 1105 and 1205. In addition, each of the wires may be devoid of gaps and discontinuities such that the body of each of the plurality of wires may extend from proximal cable 1200 to distal cable 1100 (e.g. to distal tip 1110).

Figure 2A:
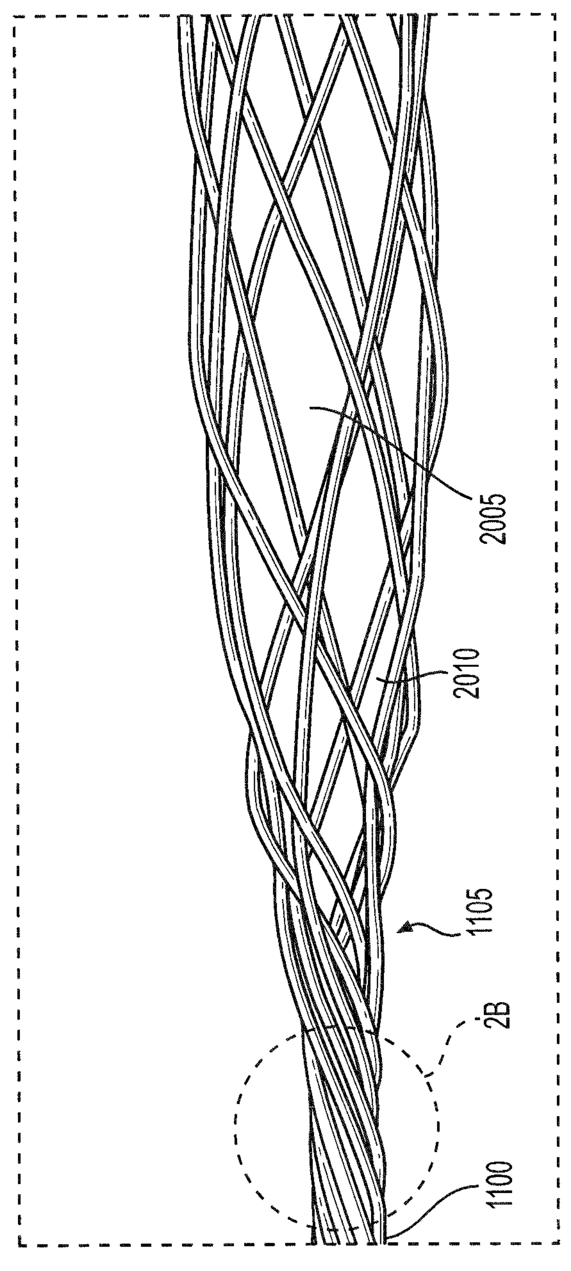
FIG. 2A illustrates an enlarged view of a distal transition region of the intraluminal device of FIG. 1, consistent with various embodiments of the present disclosure.

FIG. 2A illustrates an enlarged view of a distal transition region of intraluminal device 1000. FIG. 2A depicts transition 1105, as well as portions of distal cable 1100 and distal filter 1330. In some embodiments, due to the continuous braiding of device 1000, every wire in distal filter 1330 may extend continuously through transition 1105 to distal cable 1100 and may extend distally to distal tip 1110. As illustrated in FIG. 2A, the wires may extend through transition 1105 without interruption or gaps. Alternatively, one or more wires may be cut or otherwise severed at or near transition 1105.

As also illustrated in FIG. 2A, distal filter 1330 may have a wire weave pattern which includes a number of openings 2005, 2010 therein to capture obstructions (e.g. clots). Openings 2005, 2010 may be smaller than clot capturing windows 1316 and thus configured to capture smaller obstructions and clots than clot capturing windows 1316. In some embodiments, one or more radiopaque markers may be situated at or near transition 1105 such that the distal end of clot engaging component 1300 may be visualized, e.g. by the device operator.

In some embodiments, the wires in distal cable 1100 may be chemically or electrochemically treated to remove material therefrom, thus forming a softer and more atraumatic tip of device 1000. This may be achieved by etching, electropolishing, or any other suitable chemical or electrochemical process. By reducing the diameter of the wires in distal cable 1100, the wires may be made more pliable and soft; thus, the wires may be less damaging to tissue during use within the body.

Figure 2B:
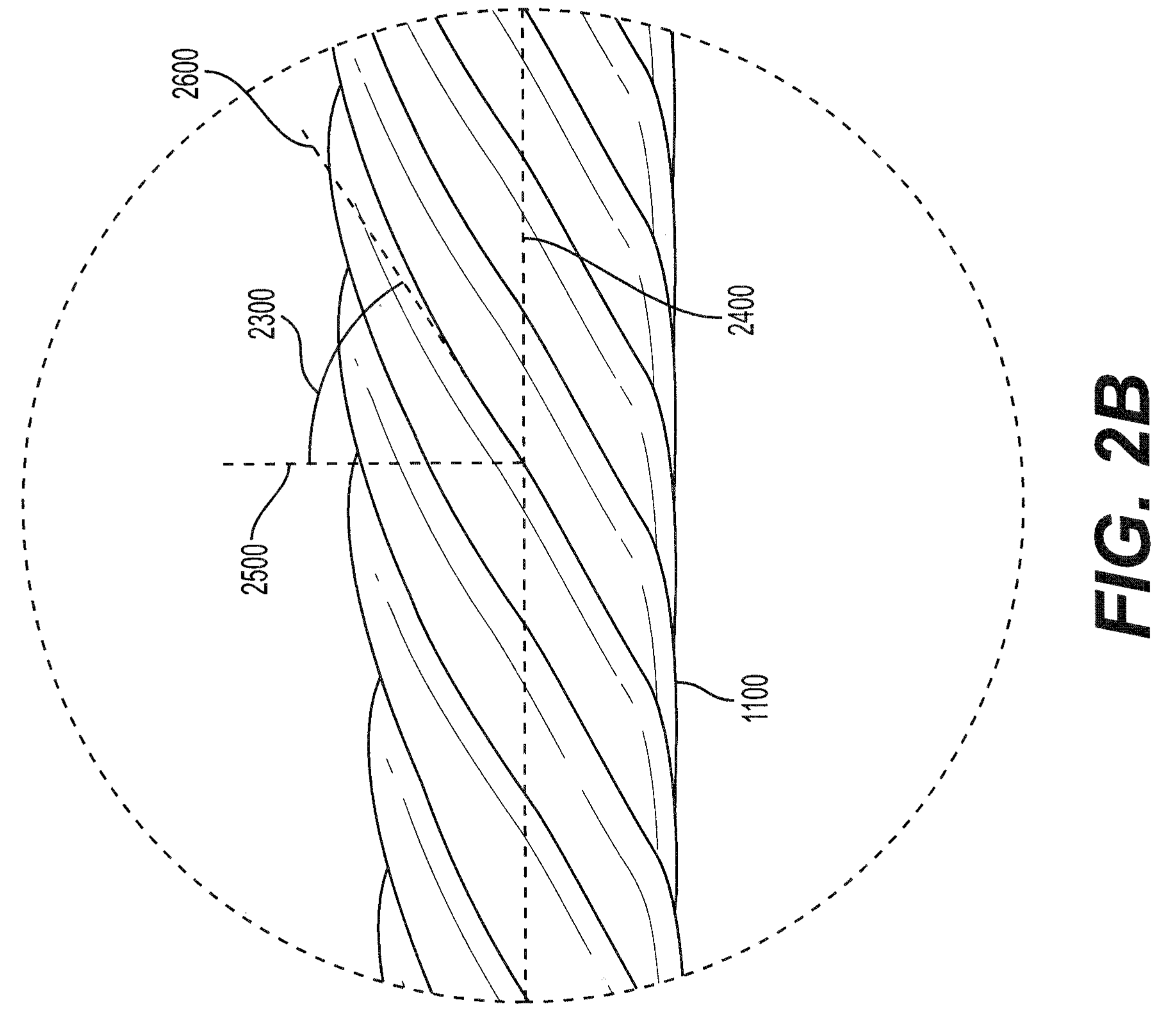
FIG. 2B illustrates an enlarged view of a distal coil of the intraluminal device of FIG. 1, consistent with various embodiments of the present disclosure.

FIG. 2B illustrates an enlarged view of distal cable 1100. As discussed above, the number and diameter of the wires in the distal cable may determine the cable coiling angle 2300. As illustrated in FIG. 2B, the cable coiling angle 2300 may be the angle formed between a direction of the wire 2600 and a lateral axis 2500, which is perpendicular to the wire axis 2400. In some embodiments, distal cable 1100 may include fewer wires (e.g. eight wires) than proximal cable 1200 (e.g. eleven or twelve wires), thus permitting a smaller cable coiling angle 2300 and thus a softer, more pliable distal cable.

Figure 3A:
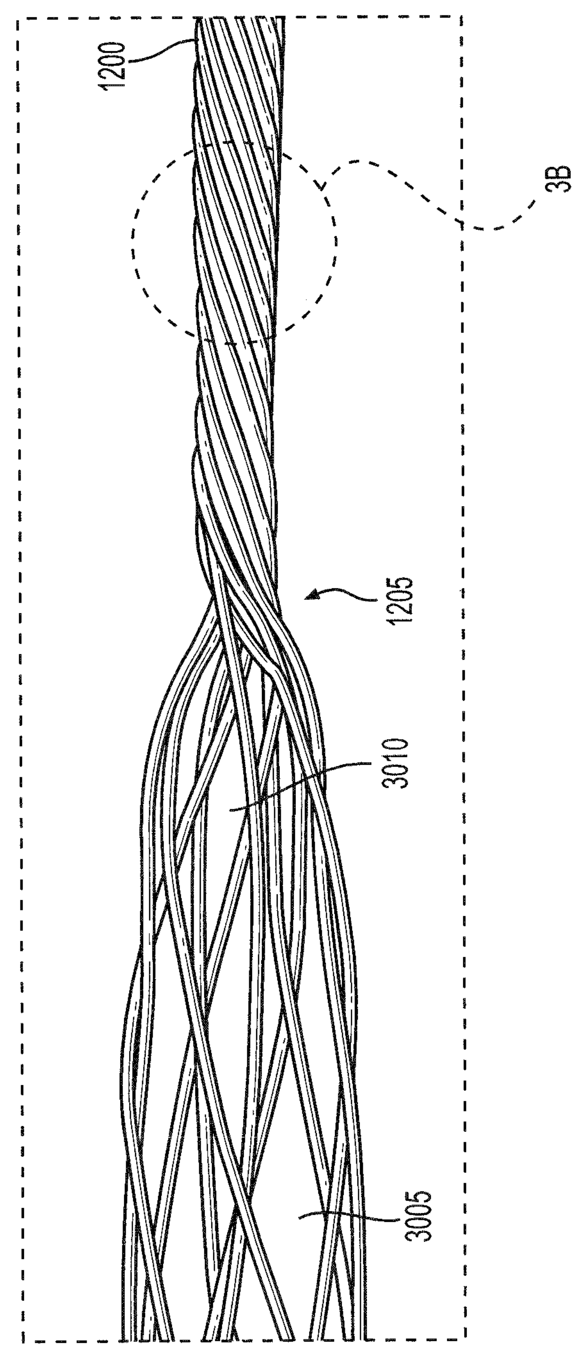
FIG. 3A illustrates an enlarged view of a proximal transition region of the intraluminal device of FIG. 1, consistent with various embodiments of the present disclosure.

FIG. 3A illustrates an enlarged view of a proximal transition region of intraluminal device 1000. FIG. 3A depicts transition 1205, as well as portions of proximal filter 1340 and proximal cable 1200. In some embodiments, due to the continuous braiding of device 1000, every wire in proximal cable 1200 may extend continuously through transition 1205 to proximal filter 1340. As illustrated in the example of FIG. 3A, the wires may extend through transition 1205 without interruption or gaps. Alternatively, one or more wires may be cut or otherwise severed at or near transition 1205.

As also illustrated in FIG. 3A, proximal filter 1340 may have a wire weave pattern including a number of openings 3005, 3010 therein to capture obstructions (e.g. clots). Openings 3005, 3010 may be smaller than clot capturing windows 1316 and thus configured to capture smaller obstructions and clots than clot capturing windows 1316. In some embodiments, one or more radiopaque markers may be situated at or near transition 1205 such that the proximal end of clot engaging component 1300 may be visualized, e.g. by the device operator.

Figure 3B:
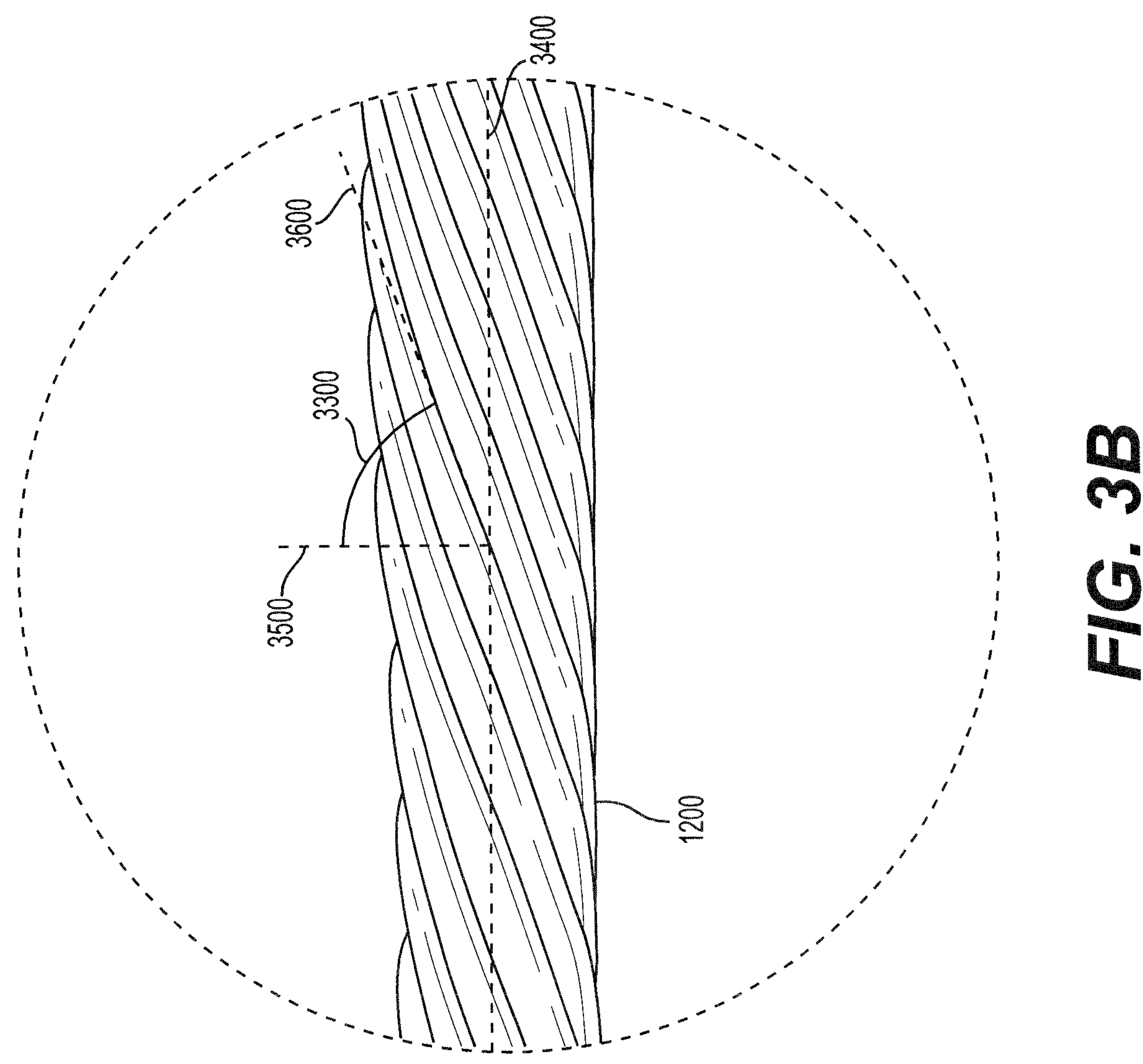
FIG. 3B illustrates an enlarged view of a proximal coil of the intraluminal device of FIG. 1, consistent with various embodiments of the present disclosure.

FIG. 3B illustrates an enlarged view of proximal cable 1200. Proximal cable 1200 may have a cable coiling angle 3300 determined by the number and diameter of the wires in the proximal cable. As illustrated in FIG. 3B, the cable coiling angle 3300 may be the angle formed between a direction of the wire 3600 and a lateral axis 3500, which is perpendicular to the wire axis 3400. In some embodiments, proximal cable coiling angle 3300 may be larger than distal cable coiling angle 2300 due to proximal cable 1200 having more wires and/or larger diameter wires than distal cable 1100. For example, distal cable coiling angle 2300 may be an angle between 5° (e.g., in a single-strand cable, as discussed below in reference to FIG. 7, with a very small angle) and 60°, while proximal cable coiling angle 3300 may be an angle between 50° and 60°. As a result, distal cable 1100 may be softer and more pliable than proximal cable 1200. In alternative embodiments, distal cable 1100 may be arranged such that distal cable coiling angle 2300 is between 60° and 70°. Without limitation, for example, distal cable coiling angle 2300 may have an angle of 1°, 2°, 3°, 4°, 5°, 8°, 10°, 12°, 15°, 20°, 25°, 30°, 35°, 40°, 45°, 50°, 55°, 60°, 65°, or 70°. In addition, and without limitation, proximal cable coiling angle 3300 may have an angle of 40°, 45°, 50°, 51°, 52°, 53°, 54°, 55°, 56°, 57°, 58 °, 59°, 60°, 65°, or 0°.

Figure 4:
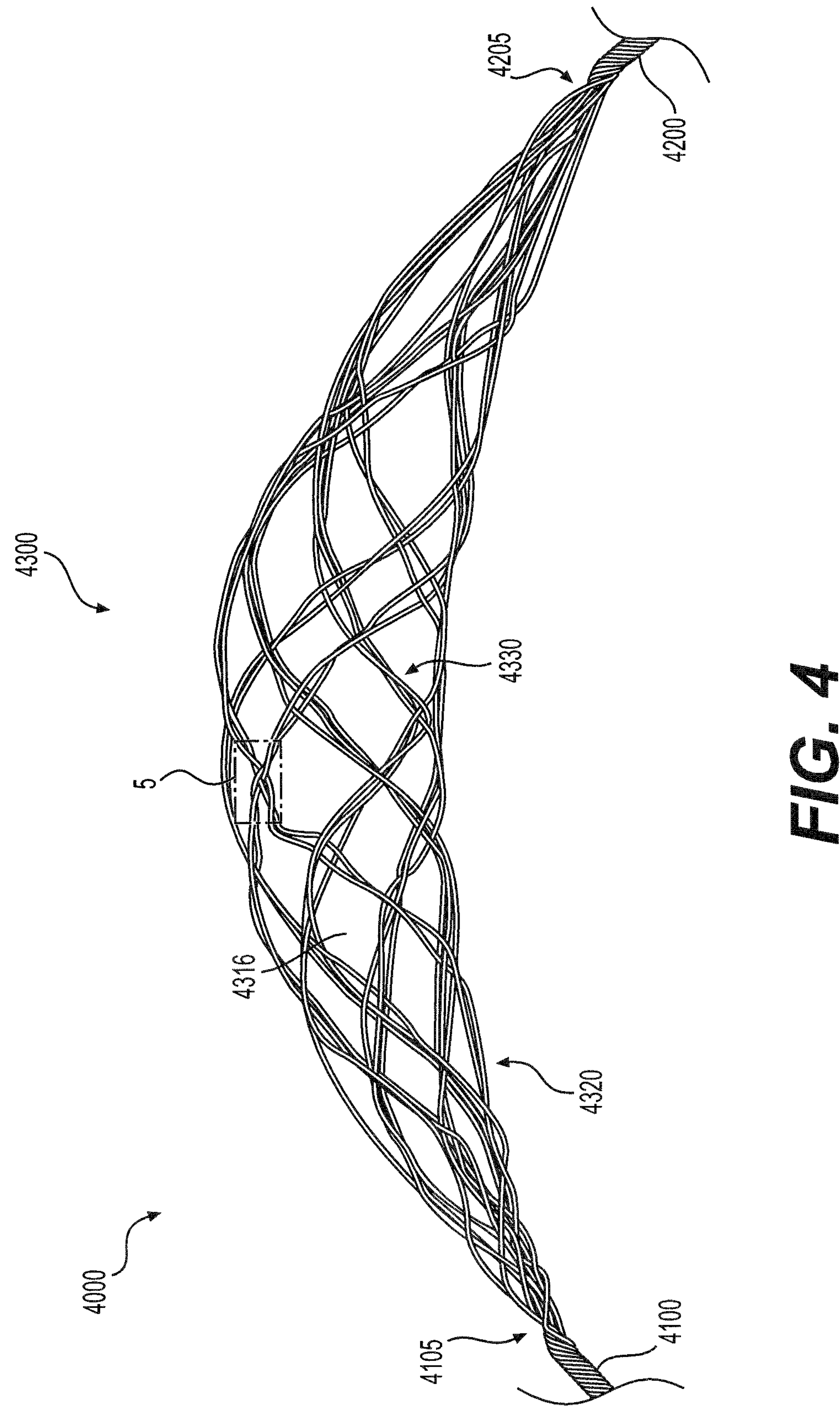
FIG. 4 illustrates another exemplary intraluminal device, consistent with various embodiments of the present disclosure.

FIG. 4 illustrates another exemplary intraluminal device 4000. Device 4000 may include a distal cable 4100, a proximal cable 4200, and an expandable clot engaging component 4300 therebetween. Device 4000 may be formed of a plurality of wires, which may be braided in the clot engaging component 4300 to form an expandable mesh-like or stent-like structure. In some embodiments, the wires may extend continuously from the proximal end of device 4000 to the distal end of device 4000, including through transitions 4105 and 4205.

Clot engaging component 4300 may include a predetermined number of wires, so as to achieve a desired mesh arrangement. Clot engaging component 4300 may include one or more pairs 4330 of coiled wires and/or one or more cables 4320 of three coiled wires. Clot capturing windows 4316 may be formed between the pairs 4330 and/or the cables 4320. For example, clot engaging component 4300 may include eight wires formed of four pairs 4330 of wires. In an alternative example, clot engaging component 4300 may include ten wires formed of two pairs 4330 of wires and two cables 4320 of wires. In a further example, clot engaging component 4300 may include twelve wires formed of four cables 4320 of wires. In a still further example, clot engaging component 4300 may include twelve wires formed of six pairs 4330 of wires. Alternatively, clot engaging component 4300 may be formed of any other suitable number of pairs 4330 of wires and/or cables 4320 of wires.

Figure 5:
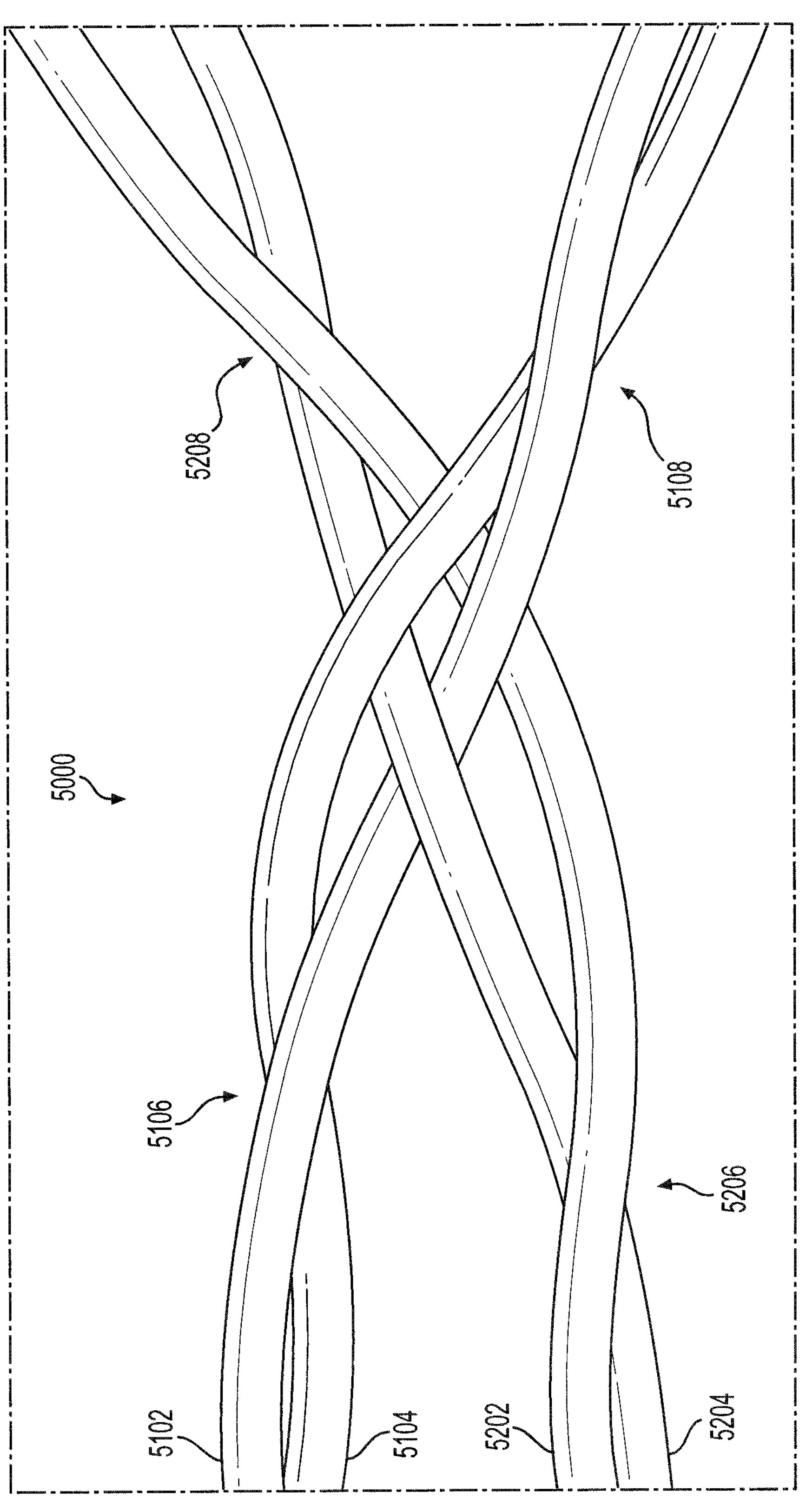
FIG. 5 illustrates an enlarged view of a wire crossing of the intraluminal device of FIG. 4, consistent with various embodiments of the present disclosure.

FIG. 5 illustrates an exemplary wire crossing 5000 of intraluminal device 4000. Crossing 5000 may be formed by the meeting of two pairs 4330 of wires at a single crossing. Each pair of wires may be twisted distal to and proximal of the crossing 5000. As illustrated in FIG. 5, wires 5102, 5104 may be twisted about each other at pairwise twist 5106 distal to the crossing and at pairwise twist 5108 proximal to the crossing. Similarly, wires 5202, 5204 may be twisted about each other at pairwise twist 5206 distal to the crossing and at pairwise twist 5208 proximal to the crossing.

In crossing 5000, each pair of wires may encircle only a single wire of the other pair of wires. For example, as illustrated in FIG. 5, wires 5102, 5104 may encircle wire 5204 at the crossing, but not wire 5202. Similarly, wires 5202, 5204 may encircle wire 5102 at the crossing, but not wire 5104.

Advantageously, this crossing arrangement may lock the two pairs of wires relative to each other, such that each pair of wires cannot slide along the other pair, while minimizing friction between the two pairs of wires due to the minimal physical engagement between the two pairs of wires. For example, crossing 5000 may be configured to function as a hinge during expansion and contraction of clot engaging component 4300, with wires 5102, 5104 configured to pivot relative to wires 5202, 5204 during expansion and contraction of component 4300, without wires 5102, 5104 sliding axially relative to wires 5202, 5204. Because of the minimal physical engagement between the two pairs of wires in crossing 5000, friction along the pivoting direction of each wire may be reduced, allowing the wires to pivot more readily and in response to lower applied forces without becoming disengaged at the crossing 5000. Advantageously, less force may be required to overcome the friction in crossing 5000 and to thus expand or contract clot engaging component 4300. In addition, no more than two wires are in contact at any given point within crossing 5000. As a result, the added thickness to the diameter of clot engaging component 4300 is no more than the sum of the diameters of the two interacting wires. Advantageously, this may permit the clot engaging component 4300 to have a minimized diameter, such as during delivery within the delivery sheath, such that device 4000 can pass through small, tortuous anatomy.

Figure 6A:
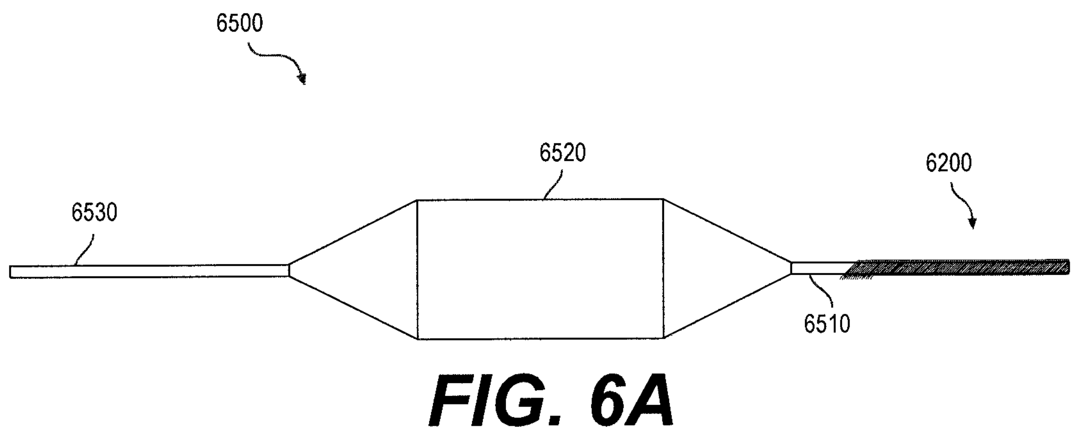
FIGS. 6A-6C depict an exemplary manufacturing method of an intraluminal device, consistent with various embodiments of the present disclosure.
Figure 6B:
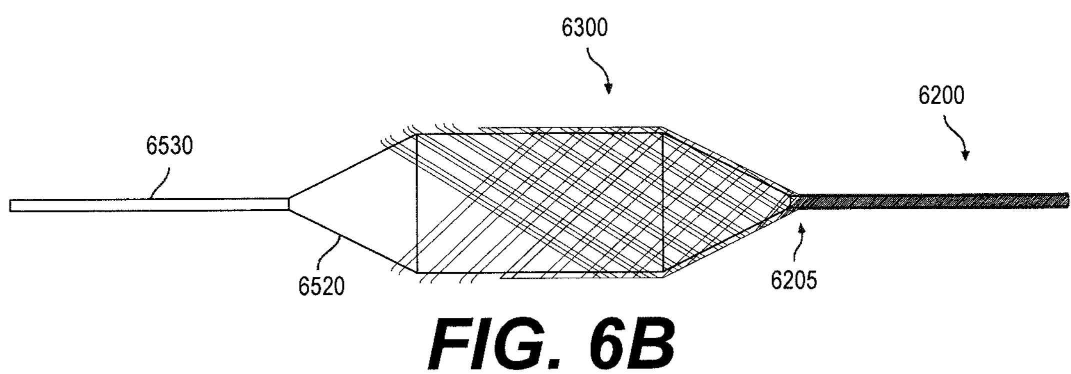
Figure 6C:
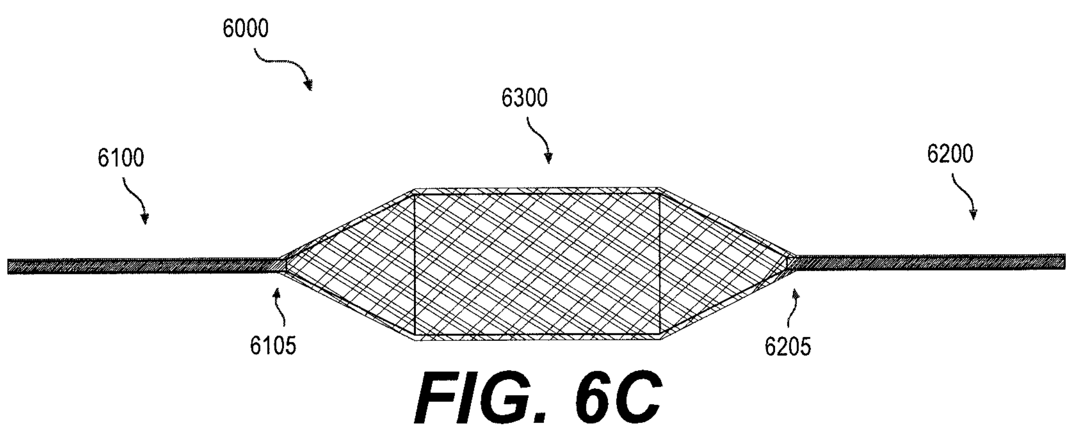

FIGS. 6A-6C depict an exemplary manufacturing method of an intraluminal device. Although the example depicted in FIGS. 6A-6C illustrates manufacturing of an exemplary intraluminal device 6000, one of ordinary skill will understand that the manufacturing method disclosed herein may be used to manufacture any suitable intraluminal device, including and not limited to intraluminal devices 1000, 4000, and 7000.

Exemplary intraluminal device 6000 may include a distal cable 6100, a proximal cable 6200, and an expandable clot engaging component 6300 therebetween. Device 6000 may be formed of a plurality of wires, which may extend continuously from the proximal end of device 6000 to the distal end of device 6000, including through transition regions 6105 and 6205. Intraluminal device 6000 may be formed by braiding the plurality of wires on a mandrel 6500. Mandrel 6500 may have a first portion 6510 upon which the proximal cable 6200 may be formed, a second portion 6520 upon which the clot engaging component 6300 may be formed, and a third portion 6530 upon which the distal cable 6100 may be formed, with each portion of mandrel 6500 having a respective shape and diameter. For example, mandrel second portion 6520 may have a larger diameter than mandrel first and third portions 6510 and 6530, respectively. As a result, clot engaging component 6300 may have a larger diameter when formed than distal and proximal cables 6100 and 6200, respectively. In some embodiments, mandrel first portion 6510 and mandrel third portion 6530 may have substantially equal diameters such that distal cable 6100 and proximal cable 6200 also have substantially equal diameters. In some alternative embodiments, mandrel first portion 6510 may have a larger or smaller diameter than mandrel third portion 6530, such that the diameters of distal cable 6100 and proximal cable 6200 are not equal. However, an exemplary mandrel 6500 consistent with the present disclosure is not limited to any particular shape, dimensions, or configuration. For example, mandrel 6500 may vary in outer dimension symmetrically or asymmetrically along its longitudinal length and may be substantially linear, curved, or a combination of both. In some embodiments, the shape, dimensions, and configuration of mandrel 6500 may be selected so as to produce a desired shape and size of intraluminal device 6000, which may be formed at least in part upon mandrel 6500.

As illustrated in FIGS. 6A-6C, the plurality of wires may be braided continuously along mandrel 6500 to form intraluminal device 6000 (including distal cable 6100, proximal cable 6200, and clot engaging component 6300) as a single unitary structure. For illustrative purposes in FIGS. 6A-6C, a slight space is shown between the wires and mandrel 6500. However, in practice, mandrel 6500 may serve as a form against which the wires may be wound. In some embodiments, such as the example depicted in FIGS. 6A-6C, the wires may be continuously braided on mandrel 6500 starting from the proximal end of intraluminal device 6000 and working distally towards the distal end of the device 6000. However, in alternative embodiments, the wires may be continuously braided from the distal end of device 6000 towards the proximal end of device 6000.

As shown in FIG. 6A, the wires may be coiled about first mandrel portion 6510 to form proximal cable 6200. Upon reaching transition region 6205 (which may be formed, in some embodiments, at or near the intersection between the first 6510 and second 6520 mandrel portions), the plurality of wires may be braided upon second mandrel portion 6520 in a mesh-like or stent-like arrangement to form clot engaging component 6300. This is depicted in FIG. 6B. In some embodiments, all of the wires forming proximal cable 6200 may pass through transition region 6205 and may extend through clot engaging component 6300; however, the braiding pattern of the wires may be different between the proximal cable 6200 and the clot engaging component 6300. Upon completing formation of clot engaging component 6300 and reaching transition region 6105 (which may be formed, in some embodiments, at or near the intersection between the second 6520 and third 6530 mandrel portions), the plurality of wires may be coiled about third mandrel portion 6530 to form distal cable 6100. In some embodiments, all of the wires forming clot engaging component 6300 may pass through transition region 6105 and may extend through distal cable 6100; however, the braiding pattern of the wires may be different between the distal cable 6100 and the clot engaging component 6300. The wires may be coiled about third mandrel portion 6100 until the distal end of device 6000 is formed; FIG. 6C depicts the completed device 6000 upon mandrel 6000.

Advantageously, the lack of connections or attachments between portions of device 6000 may result in a smoother device profile. Methods of connection, such as welding or gluing, can cause rough, protruding surface features which can scrape against tissue during use of the device within the body. Because device 6000 may lack such surface features due to the continuous braiding of the wires, the profile of the device may be smooth and therefore less traumatic during delivery through the body and during use of the device at the treatment site. In addition, the continuous braiding method may be simpler and require less time than techniques requiring the connecting of different device portions together, such as by welding.

In some embodiments, at least part of the formed intraluminal device 6000 may be heat treated before removal from mandrel 6500. In some embodiments, the entire intraluminal device 6000 may be heat treated. Alternatively, the entirety of clot engaging component 6300 may be heat treated. For example, clot engaging component 6300 may be heat treated such that the wire portions therein may have shape memory at the diameter and shape of the second mandrel portion 6520. In a further alternative, a portion of clot engaging component 6300 may be heat treated. For example, heat treatment may occur while exemplary intraluminal device 6000 remains on mandrel 6500. Heat treatment may be performed by a hot air blower directed at device 6000 or a portion thereof, or may be performed using heat applied with any other device or method. Other devices for heating or heating methods may involve convection, conduction, or both. For example, mandrel 6500 may be heated to apply heat by conduction to one or more portions of intraluminal device 6000. One example of a heat treatment may involve applying heat at at least about 450° C. to device 6000 or a portion thereof while device 6000 is maintained on mandrel 6500. In another example, a heat treatment may involve applying heat at about 500° C., or between 480° C. and 550° C., to device 6000 or a portion thereof. In yet another example, a heat treatment may be applied at any temperature which may cause the wires of device 6000 (such as the wire portions within clot engaging component 6300) to have full or partial memory of a diameter of mandrel 6500 (memory being an ability to return either partially or fully to that diameter when device 6000 is subsequently used).

Figure 7:
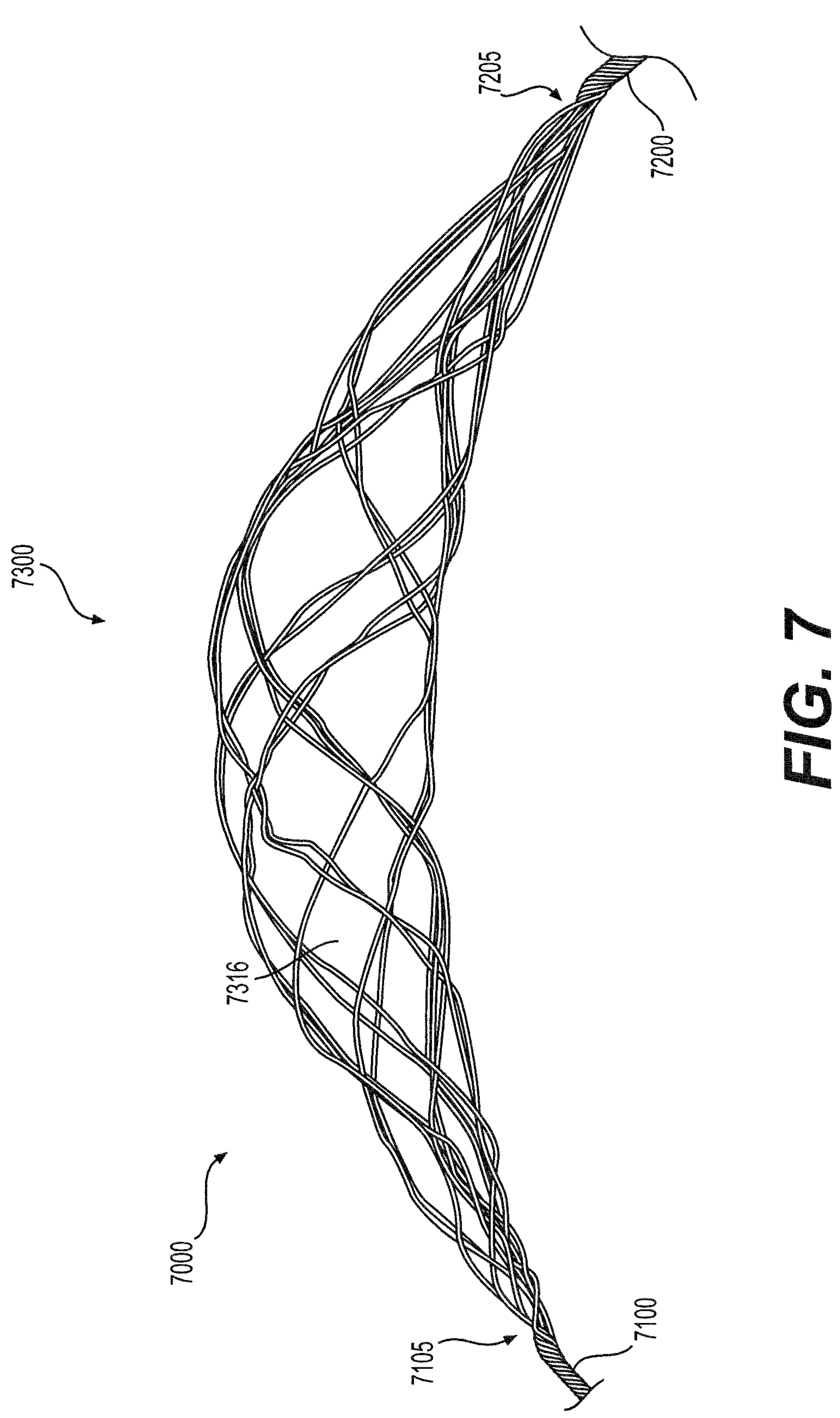
FIG. 7 illustrates a further exemplary intraluminal device, consistent with various embodiments of the present disclosure.

FIG. 7 illustrates a further exemplary intraluminal device 7000. Device 7000 may include a distal cable 7100, a proximal cable 7200, and an expandable clot engaging component 7300 therebetween. Device 7000 may be formed of a plurality of wires, which may be braided in the clot engaging component 7300 to form an expandable mesh-like or stent-like structure. In some embodiments, one or more wires of device 7000 may be cut or otherwise severed during braiding of device 7000 (for example, at transition 7105 or at transition 7205); as a result, some portions of device 7000 may have more wires than others. For example, proximal cable 7200 may have more wires than distal cable 7100 and clot engaging component 7300. Additionally or alternatively, clot engaging component 7300 may have more wires than distal cable 7100. In the example illustrated in FIG. 7, proximal cable 7200 includes fifteen wires, while distal cable 7100 and clot engaging component 7300 include twelve wires. However, one of ordinary skill will understand that the various sections of device 7000 (that is, distal cable 7100, proximal cable 7200, and clot engaging component 7300) may include any desired number of wires. For example, in some embodiments, proximal cable 7200 may have eleven wires, three of which may be cut at or near transition 7205; as a result, clot engaging component 7300 and distal cable 7100 may have eight wires. In some alternative embodiments, proximal cable 7200 may have twelve wires, four of which may be cut at or near transition 7205; as a result, clot engaging component 7300 and distal cable 7100 may have eight wires. Without limitation, for example, distal cable 7100 may have one wire, two wires, three wires, four wires, five wires, six wires, seven wires, eight wires, nine wires, ten wires, eleven wires, twelve wires, thirteen wires, fourteen wires, or fifteen wires. In addition, and without limitation, clot engaging component 7300 may have six wires, seven wires, eight wires, nine wires, ten wires, eleven wires, twelve wires, thirteen wires, fourteen wires, fifteen wires, or sixteen wires. In addition, and without limitation, proximal cable 7200 may have eight wires, nine wires, ten wires, eleven wires, twelve wires, thirteen wires, fourteen wires, fifteen wires, sixteen wires, seventeen wires, or eighteen wires.

Advantageously, incorporating different numbers of wires in segments of device 7000 may permit each segment to have distinct physical properties, including number of wires, wire diameter, cable rigidity, and braiding arrangement. As a result, each segment of device 7000 may be configured to have desired physical characteristics which may be different from the desired physical characteristics of the other segments. For example, the number of wires forming the coils of distal cable 7100 and proximal cable 7200, as well as the diameters of those wires, may determine the cable coiling angle, which affects the rigidity of the cable. Utilizing a smaller number of wires and/or smaller diameter wires may permit a smaller cable coiling angle and thus a less rigid, more pliable cable. Thus, in some embodiments distal cable 7100 may contain fewer wires and/or wires of smaller diameter than proximal cable 7200 such that distal cable 7100 is softer and less rigid than proximal cable 7200. Thus may permit device 7000 to have a soft and atraumatic distal tip and a more rigid proximal cable.

In addition, the number of wires within clot engaging component 7300 and transitions 7105, 7205 may affect the structure and physical properties of the mesh-like structure. For example, utilizing a specific number of wires within clot engaging component 7300 and transitions 7105, 7205 may allow formation of a desired mesh arrangement, including mesh size and diameter in the contracted and expanded configurations, the pattern and size of openings within clot engaging component 7300, and the deliverability of the mesh-like structure through the delivery sheath.

Moreover, the coiling angle of the wires in proximal cable 7200 may affect the tendency of cable 7200 to elongate and compress under axially-applied forces. As discussed above in reference to FIGS. 2B and 3B, the coiling angle of a cable may be the angle formed between a direction of the wires within the cable and an axis lateral to the cable. The resulting coiling angle of a cable may be a function of the diameter of the mandrel upon which the cable is formed, the number of wires in the cable, and the diameter of the wires in the cable. Specifically, utilizing a larger diameter mandrel, fewer wires, and wires with smaller diameter each contribute to reducing the coiling angle. In some embodiments, and without limitation, proximal cable 7200 may have a coiling angle of 40°, 45°, 50°, 51°, 52°, 53°, 54°, 55°, 56°, 57°, 58°, 59°, 60°, 65°, or 70°. As a result, proximal cable 7200 may resist axial deformation under applied tensile forces, instead maintaining a consistent axial length. Advantageously, during clot retrieval, this wire arrangement of proximal cable 7200 may resist axial elongation when tensile forces are applied, allowing for a smooth clot retrieval. In another example in which an elongated control member is pulled and tensioned to expand and contract clot engaging component 7300, proximal cable 7200 may resist shortening under the compression forces applied by the elongated control member.

Exemplary intraluminal device 7000 may be formed by a manufacturing method similar to that depicted in FIGS. 6A-6C, with the additional step of cutting or otherwise severing one or more wires at a predetermined portion thereof (e.g. at or near transition region 7105 and/or transition region 7205). For example, by cutting or severing at least one wire at or near transition region 7205, the number of wires extending through clot engaging component 7300 and distal cable 7100 may be reduced. One or more wires may be similarly cut or severed at or near transition region 7105. The remaining, uncut wires may be braided to form the remainder of device 7000. Alternatively, no wires may be cut at one of the transition regions 7105, 7205. In some embodiments, the ends of the cut wires may be covered by a glue or adhesive and/or covered with a marker band. As a result, any sharp edges caused by the cut wire may be covered to prevent injuries to the patient.

FIGS. 8A, 8B, 9, and 10 depict exemplary wire crossings 8000, 9000, and 10000 for wires of an exemplary intraluminal device. In some embodiments, wire crossings 8000, 9000, and 10000 may be utilized within a mesh or stent-like structure, such as clot engaging components 1300, 4300, 6300, and 7300. Wire crossings 8000, 9000, and 10000 may allow extraneous wires to be embedded or "hidden" within a wire pattern constructed of a predetermined number of wires. For example, if an eight-wire pattern is desired within a device segment but there are ten wires in the segment, one or more of exemplary wire crossings 8000, 9000, and 10000 may be utilized to embed and effectively "hide" the two extraneous wires such that the eight-wire pattern may be achieved.

Wire crossings 8000, 9000, and 10000 may provide an alternative technique to achieve device segments with different physical characteristics, as discussed above in reference with FIG. 7. For example, if an intraluminal device is desired with a twelve-wire proximal cable and a mesh segment with a nine-wire pattern, one or more of wire crossings 8000, 9000, and 10000 may be utilized in the mesh segment to embed the three extraneous wires to achieve the desired nine-wire pattern; this technique may provide an alternative to cutting or severing the three extraneous wires. Advantageously, the desired wire configurations and physical characteristics may be achieved for the different segments of the intraluminal device without needing to cut or sever any of the wires. In addition, the incorporation of wire crossings 8000, 9000, and 10000 may also permit the plurality of wires to extend continuously from the distal end of the intraluminal device to the proximal end of the intraluminal device, without connections or attachments (e.g. welding or gluing) between wires in adjacent segments.

In some embodiments, one or more of wire crossings 8000, 9000, and 10000 may be utilized in combination with cutting or severing at least one wire. For example, if an intraluminal device is desired with a ten-wire proximal cable and a mesh segment with a six-wire pattern, one wire, two wires, or three wires may be cut at the transition between the proximal cable and mesh segment. One or more of wire crossings 8000, 9000, and 10000 may be utilized in the mesh segment to embed the remaining extraneous wires to achieve the desired six-wire pattern.

Figures 8A, 8B:
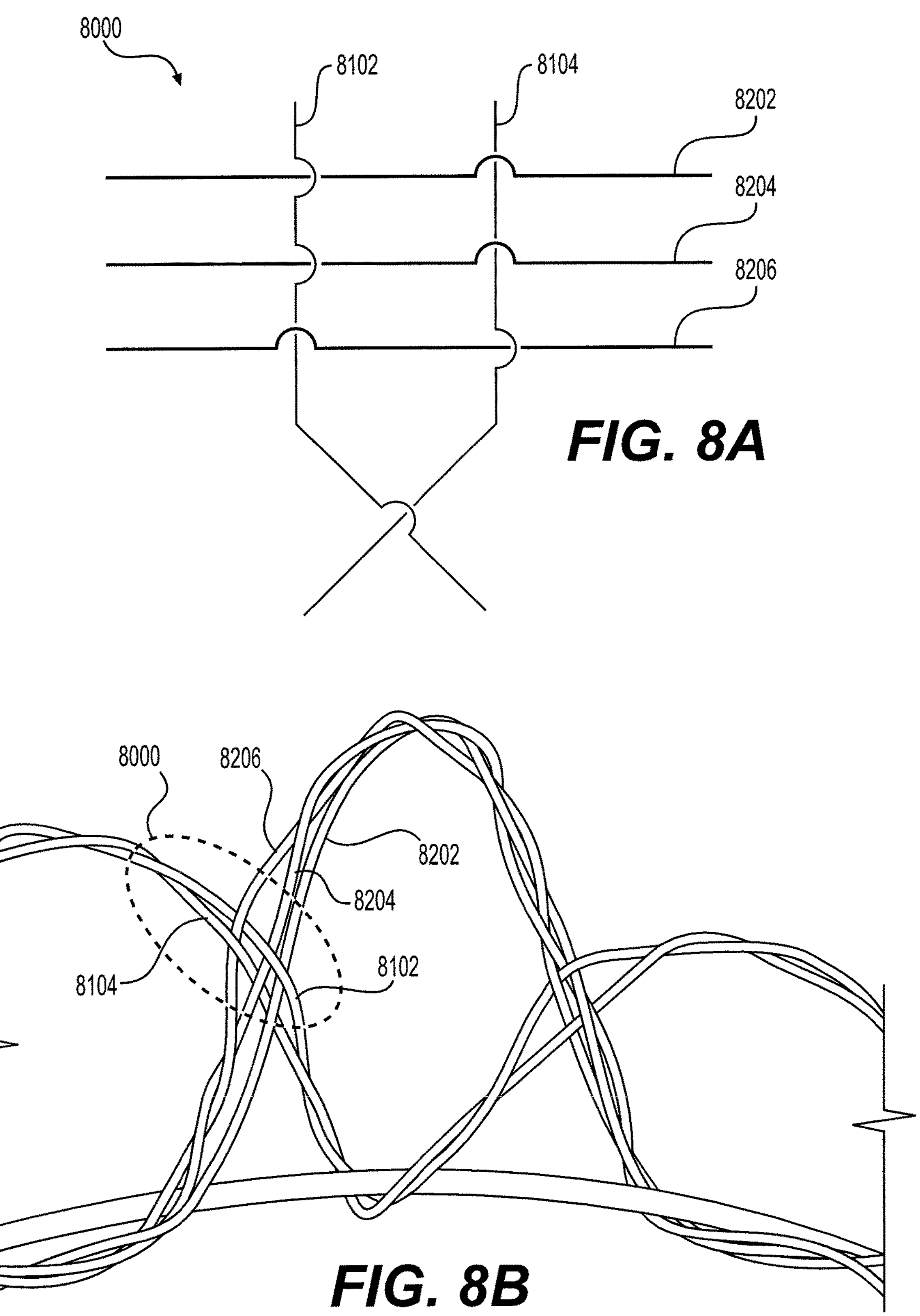
FIGS. 8A-8B depict an exemplary wire crossing of an intraluminal device, consistent with various embodiments of the present disclosure.

FIGS. 8A and 8B illustrate wire crossing 8000. In some embodiments, crossing 8000 may be utilized when one of the three wires 8202, 8204, 8206 is an extraneous wire; that is, when the desired wire pattern instead includes an intersection between two pairs of wires. Wire 8102 may cross over wires 8202, 8204 and beneath wire 8206, while wire 8104 may cross beneath wires 8202, 8204 and over wire 8206. Wire 8102 may also cross over wire 8104. As used herein, the relative terms "over" and "under" can be replaced with terminology that defines a "first side surface" of a wire, and a "second side surface" of a wire, where the "first side surface" of the wire is opposite the "second side surface." For example, as depicted in FIGS. 8A and 8B, wires 8102 and 8104 may form a first group of wires, and wires 8202, 8204, and 8206 may form a second group of wires. As shown in FIG. 8A, first wire 8102 of the first group of wires may be configured to cross the first side surfaces (for example, cross over) of first wire 8202 of the second group of wires and second wire 8204 of the second group of wires, and first wire 8102 of the first group of wires may be configured to cross the second side surface (for example, cross under) of third wire 8206 of the second group of wires. In addition, second wire 8104 of the first group of wires may be configured to cross the second side surfaces (for example, cross under) of first wire 8202 of the second group of wires and second wire 8204 of the second group of wires, and second wire 8104 of the first group of wires may be configured to cross the first side surface (for example, cross over) of third wire 8206 of the second group of wires.

Figure 9:
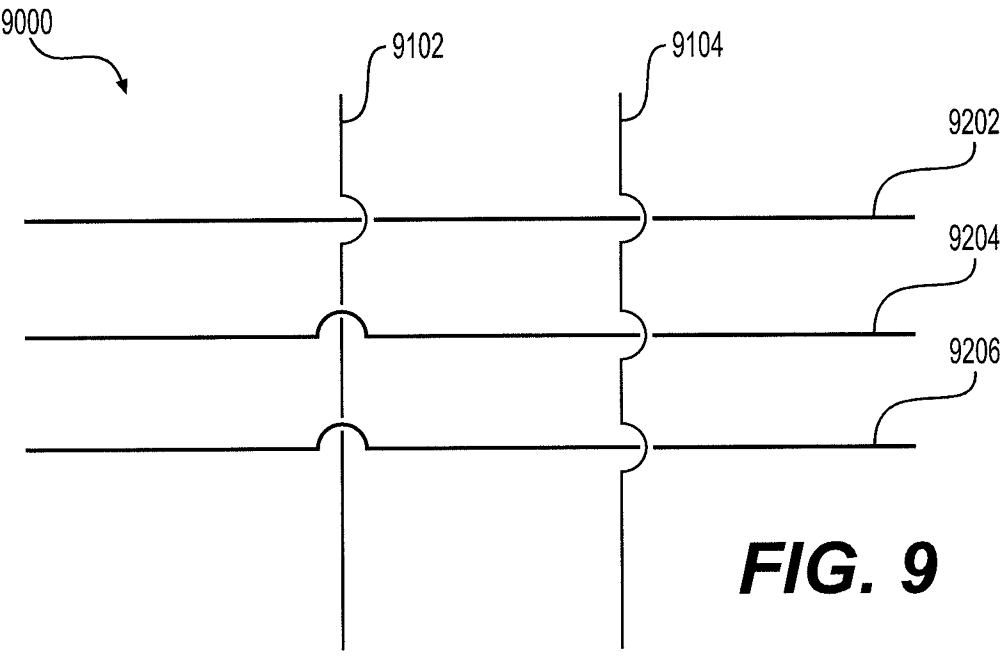
FIG. 9 depicts another exemplary wire crossing of an intraluminal device, consistent with various embodiments of the present disclosure.

FIG. 9 illustrates wire crossing 9000. In some embodiments, crossing 9000 may be utilized when one of the three wires 9202, 9204, 9206 is an extraneous wire; that is, when the desired wire pattern instead includes an intersection between two pairs of wires. For example, as depicted in FIG. 9, wires 9102 and 9104 may form a first group of wires, and wires 9202, 9204, and 9206 may form a second group of wires. As shown in FIG. 9, first wire 9102 of the first group of wires may be configured to cross the second side surfaces (for example, cross under) of second wire 9204 of the second group of wires and third wire 9206 of the second group of wires, and first wire 9102 of the first group of wires may be configured to cross the first side surface (for example, cross over) of first wire 9202 of the second group of wires. In addition, second wire 9104 of the first group of wires may be configured to cross the first side surfaces (for example, cross over) of each wire 9202, 9204, and 9206 of the second group of wires.

Advantageously, crossings 8000 and 9000 may embed or "hide" one or more extraneous wires (e.g. one or more of wires 8202, 8204, and 8206, and one or more of wires 9202, 9204, and 9206) while still configuring crossings 8000 and 9000 to function as a hinge. For example, in crossing 8000 wires 8102, 8104 may pivot relative to wires 8202, 8204, 8206 without sliding axially relative to wires 8202, 8204, 8206. Similarly, in crossing 9000 wires 9102, 9104 may pivot relative to wires 9202, 9204, 9206 without sliding axially relative to wires 9202, 9204, 9206. Crossings 8000 and 9000 may also prevent the profile of the intraluminal device from becoming enlarged from the presence of one or more extraneous wires since no more than two wires are in contact at any given point within crossings 8000 and 9000.

Figure 10:
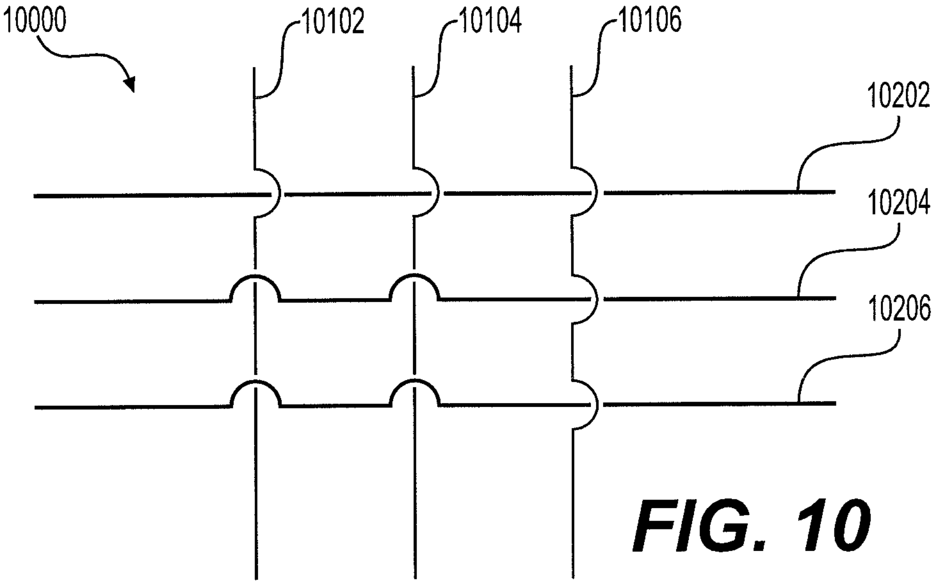
FIG. 10 depicts a further exemplary wire crossing of an intraluminal device, consistent with various embodiments of the present disclosure.

FIG. 10 illustrates wire crossing 10000. Crossing 10000 may include the intersection between a first group of three wires 10102, 10104, 10106 with a second group of three wires 10202, 10204, 10206. In some embodiments, crossing 10000 may be utilized when one of the groups of three wires includes one or more extraneous wires; for example, when the desired wire pattern instead includes an intersection between a pair of wires and a group of three wires. In some alternative embodiments, crossing 10000 may be utilized when both groups of three wires includes one or more extraneous wires; for example, when the desired wire pattern instead includes an intersection between two pair of wires, and in which one wire must be embedded or "hidden" in each group of three wires. As shown in FIG. 10, first wire 10102 of the first group of wires may be configured to cross the second side surfaces (for example, cross under) of second wire 10204 of the second group of wires and third wire 10206 of the second group of wires, and first wire 10102 of the first group of wires may be configured to cross the first side surface (for example, cross over) of first wire 10202 of the second group of wires. In addition, second wire 10104 of the first group of wires may be configured to cross the second side surfaces (for example, cross under) of second wire 10204 of the second group of wires and third wire 10206 of the second group of wires, and second wire 10104 of the first group of wires may be configured to cross the first side surface (for example, cross over) of first wire 10202 of the second group of wires. Further still, third wire 10106 of the first group of wires may be configured to cross the first side surfaces (for example, cross over) of each wire 10202, 10204, and 10206 of the second group of wires. As with crossings 8000 and 9000, crossing 10000 may permit the wires therein to function as a hinge while minimizing or preventing the enlargement of the device profile due to the presence of one or more extraneous wires.

FIGS. 11A-11B, 12A-12B, and 13A-13B respectively depict exemplary wire braiding patterns 11000, 12000, and 13000 for a group of wires of an exemplary intraluminal device. In some embodiments, wire braiding patterns 11000, 12000, and 13000 may be utilized for a group of wires within a mesh or stent-like structure (such as clot engaging components 1300, 4300, 6300, and 7300) which may include multiple groups of wires. Wire braiding patterns 11000, 12000, and 13000 may allow one or more extraneous wires in the group of wires to be embedded or "hidden" within a wire pattern of the mesh or stent-like structure, and in particular, within the portions of a wire pattern between wire crossings (that is, between the portions of a wire pattern where groups of wires intersect, such as wire crossing 5000). In some embodiments, wire braiding patterns 11000, 12000, and 13000 may be utilized in a mesh segment between one or more of wire crossings 8000, 9000, and 10000 so as to embed or "hide" one or more extraneous wires in a wire group and achieve a desired wire pattern of the mesh segment.

Figure 11A:
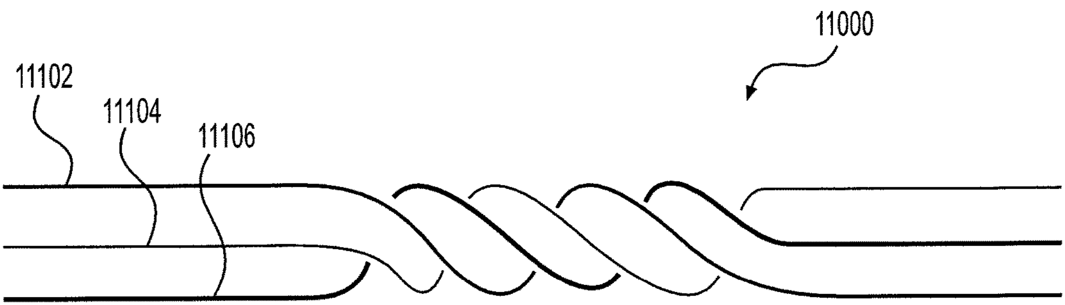
FIGS. 11A-11B depict an exemplary wire braiding pattern of an intraluminal device, consistent with various embodiments of the present disclosure.
Figure 11B:
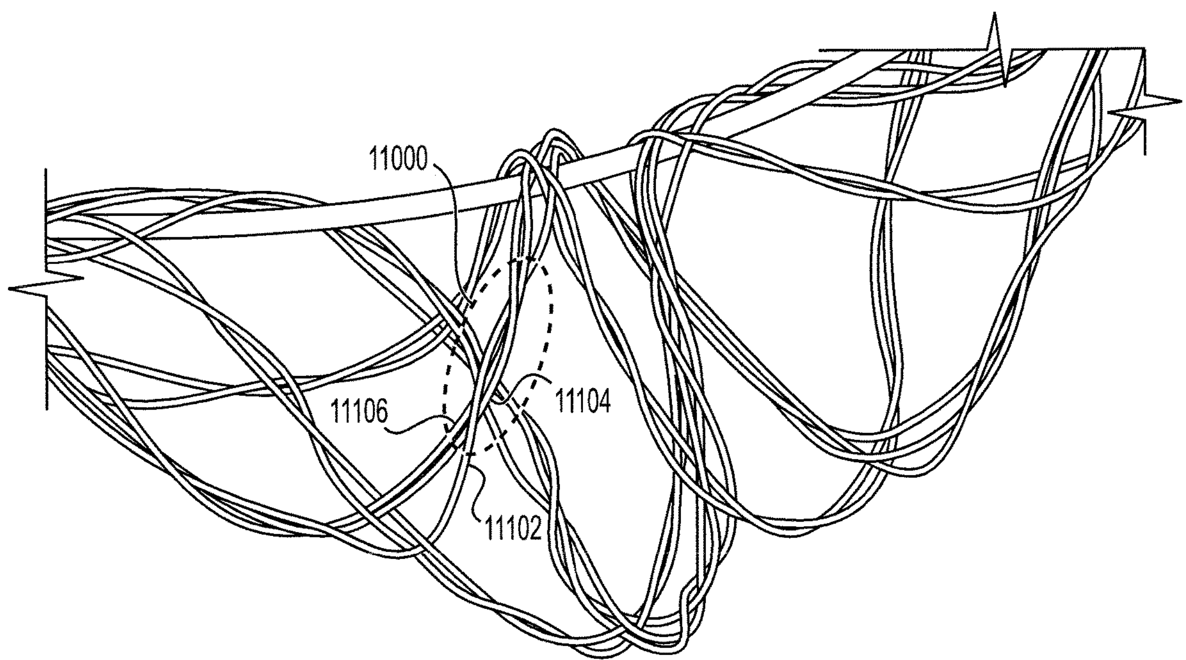

As illustrated in FIGS. 11A-11B, wire braiding pattern 11000 includes a twist of a first group of wires which may include wires 11102, 11104, and 11106. In some embodiments the term "twist" may refer to a structure in which the wires are wrapped about the others in a successive fashion. That is, wire 11102 may wrap about the other two wires, followed by wire 11104 and then wire 11106, after which wire 11102 may again wrap about the other two wires. Due to the twisting of pattern 11000, all three wires 11102, 11104, and 11106 may be secured together against inadvertent axial movement or sliding. In some embodiments, pattern 11000 may be utilized in a group of wires having one or two extraneous wires. As explained above, wires 11102, 11104, and 11106 may be twisted into pattern 11000 in a portion of the mesh segment in which wires 11102, 11104, and 11106 do not intersect with another group of wires (that is, between two adjacent crossings of the first group of wires with other groups of wires).

Figure 12A:
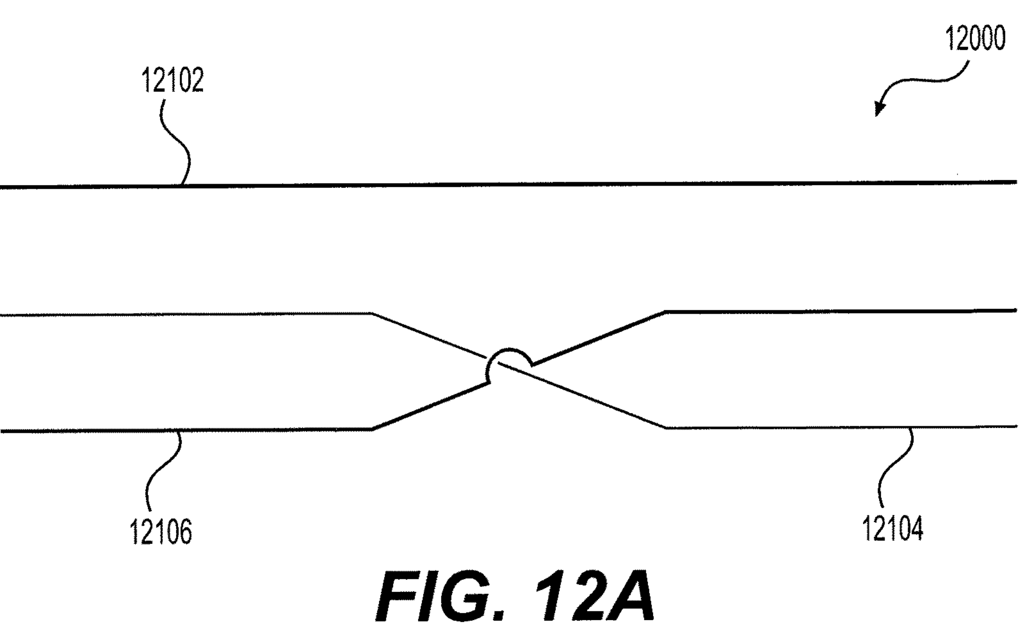
FIGS. 12A-12B depict another exemplary wire braiding pattern of an intraluminal device, consistent with various embodiments of the present disclosure.
Figure 12B:
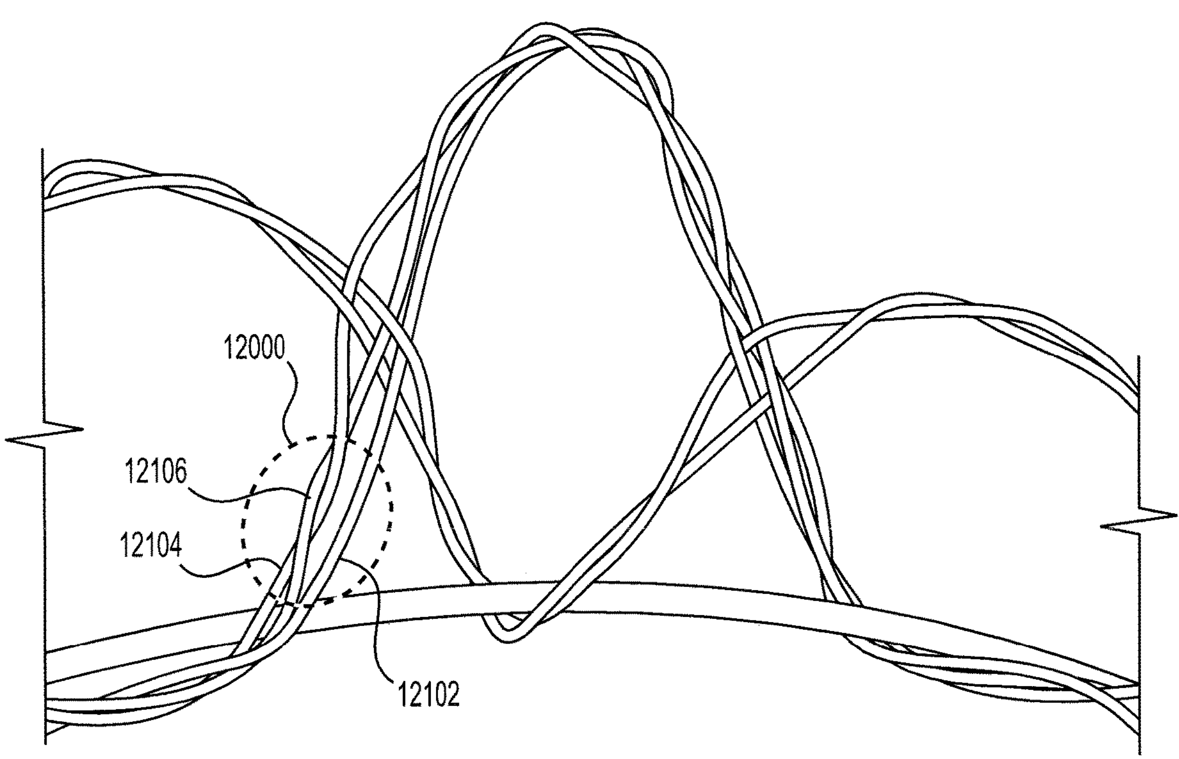

As illustrated in FIGS. 12A-12B, wire braiding pattern 12000 includes a first group of three wires 12102, 12104, and 12106. As illustrated in FIG. 12A, wires 12104, 12106 may be twisted together so as to form a twisting structure in which wires 12104, 12106 wrap about each other. Wires 12104, 12106 may be twisted in the twisting structure in a portion of the mesh segment in which wires 12102, 12104, and 12106 do not intersect with another group of wires (that is, between two adjacent crossings of the first group of wires with other groups of wires). Wire 12102, however, may be free from twisting with wire 12104 or with wire 12106 within the twisting structure of wire braiding pattern 12000.

Advantageously, pattern 12000 may secure wires 12104 and 12106 together against inadvertent axial movement or sliding, while leaving wire 12102 free to move axially without impediment. In addition, wire braiding pattern 12000 may also prevent the profile of the intraluminal device from becoming enlarged from the presence of one or more extraneous wires since no more than two wires are in contact at any given point within pattern 12000. In some embodiments, pattern 12000 may be utilized in a group of wires having one or more extraneous wires (e.g. one or more of wires 12102, 12104, or 12106).

Figure 13A:
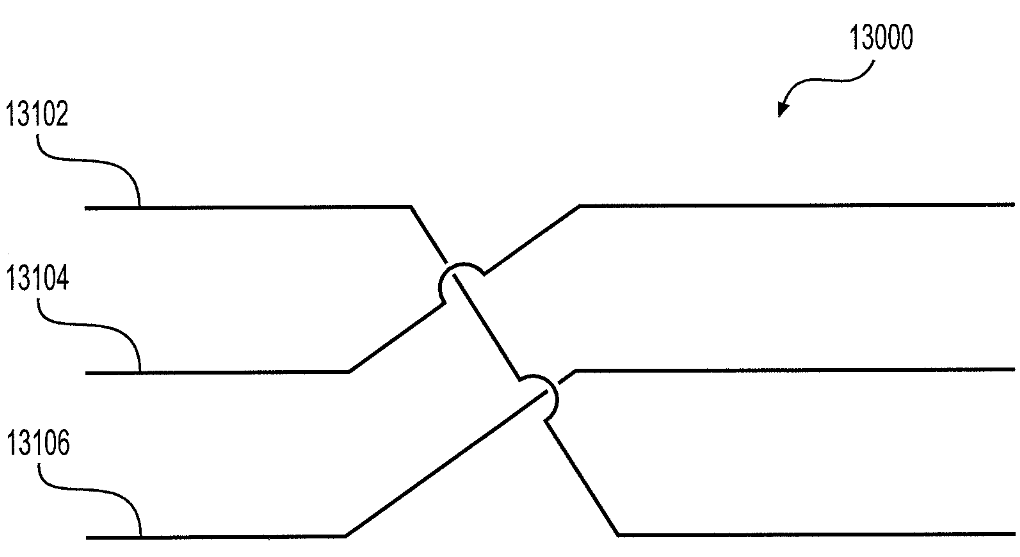
FIGS. 13A-13B depict a further exemplary wire braiding pattern of an intraluminal device, consistent with various embodiments of the present disclosure.
Figure 13B:
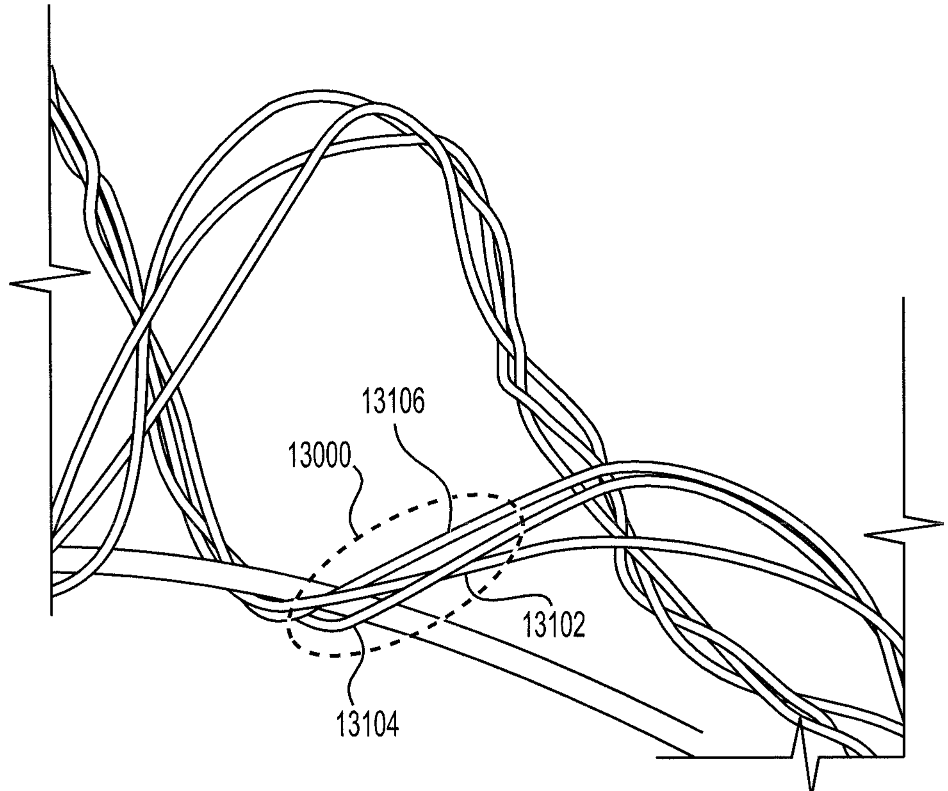

As illustrated in FIGS. 13A-13B, wire braiding pattern 13000 includes a braid pattern of a first group of three wires 13102, 13104, 13106. Wire braiding pattern 13000 may include an interlocking maypole structure of wires 13102, 13104, 13106. As depicted in FIG. 13A, within the interlocking maypole structure, first wire 13102 may be configured to cross the second side surface (for example, cross under) of second wire 13104. In addition, first wire 13102 may be configured to cross the first side surface (for example, cross over) of third wire 13106. However, second wire 13104 and third wire 13106 do not contact or cross the other in the interlocking maypole structure of pattern 13000. The interlocking maypole structure of pattern 13000 may be formed in a portion of the mesh segment in which wires 13102, 13104, 13106 do not intersect with another group of wires (that is, between two adjacent crossings of the first group of wires with other groups of wires). Advantageously, pattern 13000 may secure wires 13102, 13104, and 13106 against axial movement or sliding relative to one another, and may also prevent the profile of the intraluminal device from becoming enlarged from the presence of one or more extraneous wires since no more than two wires are in contact at any given point within pattern 13000. In some embodiments, pattern 13000 may be utilized in a group of wires having one or more extraneous wires (e.g. wire 13102, wire 13104, and/or wire 13106).

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. While certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. An intraluminal device including an elongated body formed of a plurality of wires, the intraluminal device comprising:

a first region wherein the plurality of wires are twisted to form a first cable;

a second region, distal to the first region, in which the plurality of wires are woven to form an expandable mesh segment which is configured to capture a blood clot; and a third region distal to the second region and forming a distal tip of the elongated body, wherein the plurality of wires in the third region are twisted to form a second cable, wherein each of the wires extends continuously from the first region, through the second region to the third region providing a smooth device profile;

wherein the second region includes one or more wire crossings where one or more extraneous wires of the plurality of wires, adjacent to a different wire of the plurality of wires, is embedded by following a weave pattern of the different wire;

wherein the one or more wire crossings includes a crossing of a first grouping of wires and a second grouping of wires;

wherein the first grouping of wires include at least three wires, including the one or more extraneous wires;

wherein wires of the first grouping of wires excluding the one or more extraneous wires are twisted together to provide at least one twist at least one location away from the crossing.

2. The intraluminal device of claim 1, wherein the plurality of wires extend continuously from the first region, through the second region, to and through the third region to the distal tip.

3. The intraluminal device of claim 1, wherein the first region of the intraluminal device, the second region of the intraluminal device, and the third region of the intraluminal device are formed as a single unitary structure.

4. The intraluminal device of claim 1, wherein the plurality of wires form a plurality of groupings of wires in the second region, and wherein the at least one extraneous wire is embedded in a first grouping of wires of the plurality of groupings of wires.

5. The intraluminal device of claim 4, wherein the plurality of groupings of wires includes the first grouping of wires and a second grouping of wires, the first grouping of wires including three wires and the second grouping of wires including two wires.

6. The intraluminal device of claim 1, wherein at the one or more wire crossings the intraluminal device includes a first grouping of wires and a second grouping of wires, the first grouping of wires including at least two wires and the second grouping of wires including the one or more extraneous wires and the different wire; and wherein the one or more extraneous wires and the different wire pass over a first wire of the first grouping of wires and under a second wire of the first grouping of wires to embed the one or more extraneous wire.

7. The intraluminal device of claim 6, wherein the second grouping of wires comprises a third wire, the first wire of the first grouping of wires crossing under the third wire of the second grouping of wires; and the second wire of the first grouping of wires crossing over the third wire of the second grouping of wires.

8. The intraluminal device of claim 6, wherein, at a subsequent crossing, the one or more extraneous wire and the different wire both pass over one of the wires of the first grouping of wires and under another of the wires of the second grouping of wires.

9. The intraluminal device of claim 1, comprising an elongated control member configured to apply force to the intraluminal device to affect expansion or contraction of the second region.

10. The intraluminal device of claim 1, wherein a number of the plurality of wires is selected to provide a desired rigidity to the first region.

11. The intraluminal device of claim 10, wherein the number of the plurality of wires is selected to provide a desired coiling angle in the first region, the desired coiling angle providing the desired rigidity of the first region.

12. The intraluminal device of claim 1, comprising a filter region adjacent to the second region, wherein a second region weave pattern provides a larger diameter to the second region in an expanded configuration than a weave pattern of the filter region which provides a smaller diameter to the filter region in the expanded configuration.

13. The intraluminal device of claim 1, wherein the at least one twist secures twisted wires of the first grouping against axial movement while leaving the one or more extraneous wire free to move axially.

14. A method of manufacturing an intraluminal device including an elongated body formed of a plurality of wires, the method comprising:

twisting a plurality of wires upon a first segment of a mandrel so as to form a first cable of the elongated body;

weaving each of the wires upon a second segment of the mandrel distal to the first segment, the weaving including forming one or more wire crossings with the plurality of wires, so as to form an expandable mesh segment of the elongated body which is configured to capture a blood clot, wherein the weaving comprises embedding one or more extraneous wires of the plurality of wires, adjacent to a different wire of the plurality of wires, by following a weave pattern of the different wire;

wherein the forming one or more wire crossings comprises crossing a first grouping of wires and a second grouping of wires;

wherein the first grouping of wires includes at least three wires, including the one or more extraneous wires;

wherein the forming comprises twisting together wires of the first grouping of wires excluding the one or more extraneous wires to provide at least one twist at least one location away from the crossing; and twisting each of the plurality of wires upon a third segment of the mandrel so as to form a second cable of the elongated body, each wire of the plurality of wires extending continuously from the first cable, through the expandable mesh segment, to the second cable, providing a smooth device profile;

wherein the second segment of the mandrel is positioned between the first segment of the mandrel and the third segment of the mandrel.

15. The method of claim 14, further comprising heat-treating the expandable mesh segment.

* * * * *